United States Patent
Pulé et al.

(10) Patent No.: US 12,187,769 B2
(45) Date of Patent: Jan. 7, 2025

(54) CELL

(71) Applicant: AUTOLUS LIMITED, London (GB)

(72) Inventors: Martin Pulé, London (GB); Shaun Cordoba, London (GB); Simon Thomas, London (GB); Shimobi Onuoha, London (GB); Matteo Righi, London (GB)

(73) Assignee: AUTOLUS LIMITED, London (GB)

(*) Notice: Subject to any disclaimer, the term of this patent is extended or adjusted under 35 U.S.C. 154(b) by 0 days.

(21) Appl. No.: 18/323,090

(22) Filed: May 24, 2023

(65) Prior Publication Data
US 2024/0075066 A1 Mar. 7, 2024

Related U.S. Application Data

(62) Division of application No. 16/646,906, filed as application No. PCT/GB2018/052583 on Sep. 12, 2018, now Pat. No. 11,701,386.

(30) Foreign Application Priority Data

Sep. 13, 2017 (GB) ..................... 1714718

(51) Int. Cl.
| | |
|---|---|
| C12N 15/62 | (2006.01) |
| A61K 35/17 | (2015.01) |
| A61K 39/00 | (2006.01) |
| C07K 14/47 | (2006.01) |
| C07K 14/705 | (2006.01) |
| C12N 5/0783 | (2010.01) |

(52) U.S. Cl.
CPC ...... *C07K 14/4705* (2013.01); *A61K 39/4611* (2023.05); *A61K 39/4631* (2023.05); *A61K 39/464404* (2023.05); *A61K 39/464412* (2023.05); *C07K 14/705* (2013.01); *C12N 5/0637* (2013.01); *C12N 15/62* (2013.01); A61K 2239/31 (2023.05); A61K 2239/47 (2023.05); C07K 2319/02 (2013.01); C07K 2319/20 (2013.01); C07K 2319/50 (2013.01); C07K 2319/70 (2013.01)

(58) Field of Classification Search
CPC .... A61K 35/17; C07K 14/47; C07K 14/4705; C07K 2319/70; C12N 15/62
See application file for complete search history.

(56) References Cited

U.S. PATENT DOCUMENTS

| | | |
|---|---|---|
| 2022/0025001 A1 | 1/2022 | Sentman et al. |
| 2022/0145325 A1 | 5/2022 | Pulé et al. |
| 2022/0364116 A1 | 11/2022 | Pulé et al. |

FOREIGN PATENT DOCUMENTS

| | | |
|---|---|---|
| WO | WO-01/09326 A1 | 2/2001 |
| WO | WO-2015/150771 A1 | 10/2015 |
| WO | WO-2017/029512 A1 | 2/2017 |
| WO | WO-2017/190100 A1 | 11/2017 |
| WO | WO-2017/218850 A1 | 12/2017 |
| WO | WO-2020/183131 A1 | 9/2020 |

OTHER PUBLICATIONS

Eyquem et al., Nature, 543, 113-117, Mar. 2017.*
Baker et al., "Hematopoietic cytokine receptor signaling," Oncogene 26:6724-6737 (2007).
Burchill et al., "Distinct Effects of STAT5 Activation on CD4+ and CD8+ T Cell Homeostasis: Development of CD4+ CD25+ Regulatory T Cells versus CD8+ Memory T Cells", The Journal of Immunology, 171(11):5853-5864 (2003).
Ding et al., "IL-7 signaling imparts polyfunctionality and stemness potential to CD4+ T cells," Oncoimmunology 5(6):e1171446, 13 pages (2016).
Hassuneh et al., "Evidence for the Participation of Interleukin-2 (IL-2) and IL-4 in the Regulation of Autonomous Growth and Tumorigenesis of Transformed Cells of Lymphoid Origin," Blood 89:610-620 (1997).
Hurton et al., "Tethered IL-15 augments antitumor activity and promotes a stem-cell memory subset in tumor-specific T cells," PNAS 113(48):E7788-E7797 (2016).
International Search Report and Written Opinion from International Application No. PCT/GB2018/052583 dated Nov. 23, 2018.
Kagoya et al., "A novel chimeric antigen receptor containing a JAK-STAT signaling domain mediates superior antitumor effects," Nat Med 24(3):352-359 (2018).
Milner et al., "Early-onset lymphoproliferation and autoimmunity caused by germline STAT3 gain-of-function mutations," Blood 125:591-599 (2015).
Nagarkatti et al., "Constitutive activation of the interleukin 2 gene in the induction of spontaneous in vitro transformation and tumorigenicity of T cells," Proc. Natl. Acad. Sci. 91:7638-7642 (1994).
Onishi et al., "Identification and Characterization of a Constitutively Active STAT5 Mutant That Promotes Cell Proliferation," Molecular and Cellular Biology 18(7):3871-3879 (1998).
Vogtenhuber et al., "Constitutively active Stat5b in CD4+ T cells inhibits graft-versus-host disease lethality associated with increased regulatory T-cell potency and decreased T effector cell responses," Blook 116(3):466-474 (2010).

* cited by examiner

*Primary Examiner* — Maryam Monshipouri
(74) *Attorney, Agent, or Firm* — MARSHALL, GERSTEIN & BORUN LLP

(57) ABSTRACT

The present invention relates to a cell comprising a chimeric antigen receptor (CAR) and a constitutively active or inducible Signal Transducer and Activator of Transcription (STAT) molecule.

5 Claims, 18 Drawing Sheets

Specification includes a Sequence Listing.

Figure 7

SEQ ID NO: 7 (STAT3 – Linker – STAT5)

STAT3:MAQWNQLQQLDTRYLEQLHQLYSDSFPMELRQFLAPWIESQDWAYAASKESHATLVFHNLLGEIDQQYSRFLQESNVLYQHNLRRIKQFL
QSRYLEKPMEIARIVARCLWEESRLLQTAATAAQQGGQANHPTAAVVTEKQQMLEQHLQDVRKRVQDLEQKMKVVENLQDDFDFNYKTLKSQGDMQ
DLNGNNQSVTRQKMQQLEQMLTALDQMRRSIVSELAGLLSAMEYVQKTLTDEELADWKRRQQIACIGGPPNICLDRLENWITSLAESLQTRQQIK
KLEELQQKVSYKGDPIVQHRPMLEERIVELFRNLMKSAFVVERQPCMPMHPDRPLVIKTGVQFTTKVRLLVKFPELNYQLKIKVCIDKDSGDVAAL
RGSRKFNILGTNTKVMNMEESNNGSLSAEFKHLTLREQRCGNGGRANCDASLIVTEELHLITFETEVYHQGLKIDLETHSLPVVVISNICQMPNAW
ASILWYNMLTNNPKNVNFFTKPPIGTWDQVAEVLSWQFSSTTKRGLSIEQLTTLAEKLLGPGVNYSGCQITWAKFCKENMAGKGFSFWWLDNIID
LVKKYILALWNEGYIMGFISKERERAILSTKPPGTFLLRFSESSKEGGVTFTWVEKDISGKTQIQSVEPYTKQQLNNMSFAEIMGYKIMDATNIL
VSPLVYLYPDIPKEEAFGKYCRPESQEHPEADPGSAAPYLKTKFICVTPTTCSNTIDLPMSPRTLDSLMQFGNNGEGAEPSAGGQFESLTFDMELT
SECATSPM

Linker: SGGGGSGGGGSGGGGSGGGGSGGGGS

STAT5:MAGWIQAQQLQGDALRQMVLYGQHFPIEVRHYLAQWIESQPWDAIDLDNPQDRAQATQLLEGLVQELQKKAEHQVGEDGFLLKIKLGHY
ATQLQKTYDRCPLELVRCIRHILYNEQRLVREANNCSSPAGILVDAMSQKHLQINQTFEELRLVTQDTENELKKLQQTQEYFIIQYQESLRIQAQF
AQLAQLSPQERLSRETALQQKQVSLEAWLQREAQTLQQYRVELAEKHQKTLQLLRKQQTIILDDELIQWKRRQQLAGNGGPPEGSLDVLQSWCEKL
AEIIWQNRQQIRRAEHLCQQLPIPGPVEEMLAEVNATITDIISALVTSTFIIEKQPPQVLKTQTKFAATVRLLVGGKLNVHMNPPQVKATIISEQQ
AKSLLKNENTRNECSGEILNNCCVMEYHQATGTLSAHFRNMSLKRIKRADRRGAESVTEEKFTVLFESQFSVGSNELVFQVKTLSLPVVIVHGSQ
DHNATATVLWDNAFAEPGRVPFAVPDKVLWPQLCEALNMKFKAEVQSNRGLTKENLVFLAQKLFNNSSSHLEDYSGLSVSWSQFNRENLPGWNYTF
WQWFDGVMEVLKKHHKPHWNDGAILGFVNKQQAHDLLINKPDGTFLLRFSDSEIGGITIAMKFDSPERNLWNLKPFTTRDFSIRSLADRLGDLSYL
IYVFPDRPKDEVFSKYTPVLAKAVDGYVKPQIKQVVPEFVNASADAGGSSATYMDQAPSPAVCPQAPYNMYPQNPDHVLDQDGEFDLDETMDVAR
HVEELLRRPMDSLDSRLSPPAGLFTSARGSLS

Figure 8

SEQ ID NO: 8 (TIP – STAT3 – Linker – STAT5 – 2a – Myristoylation and palmitoylation sequence – Ridge Linker – TetRB)

TIP:MWTWNAYAFAAP
Linker:SGGGS
STAT3:AQWNQLQQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLMEESRLLQTAATAAQQGQANHPTAAVTEKQQMLEQHLQDVRKRVQDLEQKMKVVENLQDDFENYKTLKSQGDMQDLNGNNQSVTRQKMQQLEQ
MLTALDQMRRSIVSELAGLLSAMEYVQKTLTDEELADWKRRQIACIGGPPNICLDRLENWITSLAESQLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKENILGTNTKVMNEESNNGLSAEFKHLTLRE
QRCGNGGRANCDASLIVTEELHLITFETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWVWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNILVSPLVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM Linker:
SGGGGSGGGGSGGGGSGGGGSGGGGS STAT5:
MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYDRCPLEL
VRCIRHILYNEQRLVREAANNCSSPAGILVDAMSQKHLQINQTFEELRLVTQDTENELKKLQQTQEYFIIQYQESLRIQAQFAQLAQLSPQERLSRETALQQKQVS
LEAWLQREAQTLQQYRVELAEKHQKTLQLLRKQQTIILDDELIQWKRRQQLAGNGGPPEGSLDVLQSWCEKLAEIIWQNRQQIRRAEHLCQQLPIPGPVEEMLAE
VNATITDIISALVTSTFIIEKQPPQVLKTQTKFAATVRLLVGGKLNVHMNPPQVKATIISEQQAKSLLKNENTRNECSGEILNNCCVMEYHQATGTLSAHFRNMS
LKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEVQSNRGL
TKENLVFLAQKLFNNSSSHLEDYSGLSVSWSQFNRENLPGWNYTFWQWFDGVMEVLKKHHKPHWNDGAILGFVNKQQAHDLLINKPDGTFLLRFSDSEIGGITIA
WKFDSPERNIWNLKPFTTRDFSIRSLADRLGDLSYLIYVFPDRPKDEVFSKYYTPVLAKAVDGYVKPQIKQVVPEFVNASADAGGSSATYMDQAPSPAVCPQAPY
NMYPQNPDHVLDQDGEFDLDETMDVARHVEELLRRPMDSLDSRLSPPAGLFTSARGSLS 2A:EGRGSLLTCGDVEENPGP
Myristoylation and Palmitoylation sequence (10aa_Lck):MGCGCSSHPE
Ridge linker:LEAEAAAKEAAAAKEAAAAKEAAAAKALEAEAAAKEAAAAKEAAAAKEAAAAKALESGGGS
TetRb:MSRLDKSKVINSALELLNEVGIEGLTTRKLAQKLGVEQPTLYWHVKNKRALLDALAIEMLDRHHTHFCPLEGESWQDFLRNNAKSFRCALLSHRDGAKV
HLGTRPTEKQYETLENQLAFLCQQGFSLENALYALSAVGHFTLGCVLEDQEHQVAKEERETPTTDSMPPLLRQAIELFDHQGAEPAFLFGLELIICGLEKQLKCE
SGS

Figure 9

SEQ ID NO: 9 (SH2 ZAP70 – Linker – TEV – 2a – Myristoylation and palmitoylation sequence – linker – TEV cleavage site – STAT3 – Linker – STAT5 – 2a – aCD19)

DZap70SH2domains: MPDPAAHLPFFYGSISRAEAEEHLKLAGMADGLFLLRQCLRSLGGYVLSLVHDVRFHHFPIERQLNGTYAIAGGKAHCGPAELCEFYS
RDPDGLPCNLRKPCNRPSGLEPQPGVFDCLRDAMVRDYVRQTWKLEGEALEQAIISQAPQVEKLIATTAHERMPWYHSSLTREEAERKLYSGAQTDGKFLLRPRK
EQGTYALSLIYGKTVYHYLISQDKAGKYCIPEGTKFDTLWQLVEYLKLKADGLIYCLKEACPNSSASNASGAAAPTLPAHPSTLTHP Linker: SGGGGS TEV: SLFKGPRDYNPISSTICHLTNESDGHTTSLYGIGFGPFIITNKHLFRRNNGTLLVQSLHGVFKVKNTTTLQQHLIDGRDMIIRMPKDFPFPQKLKFREP
QREERICLVTTNFQTKSMSSMVSDTSCTFPSSDGIFWKHWIQTKDGQCGSPLVSTRDGFIVGIHSASNFTNTNNYFTSVPKNFMELLTNQEAQQWVSGWRLNADS
VLWGGHKVFMSKPEEFQPVKEATQLMNELVYSQ

2A: EGRGSLLTCGDVEENPGP

Myristoylation and Palmitoylation sequence (10aa_Lck): MGCGCSSHPE

Linker: SGGGSGGGGS

TEV cleavage site x3: ENLYFQGENLYFQGENLYFQG

STAT3: AQWNQLQQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQQGQANHPTAAVTEKQQMLEQHLQDVRKRVQDLEQMKVVENLQDDFDENYKTLKSQGDMQDLNGNNQSVTRQKMQQLEQ
MLTALDQMRRSIVSELAGLLSAMEYVQKTLTDEELADWKRRQQIACIGGPPNICLDRLENWITSLAESLQTRQQIKKLEELQQKVSYKGDPIVQHRPMLEERIV
ELFRNLMKSAFVVERQPCMPMHPDRPLVIKTGVQFTKVFLLVKFPELNYQLKIKVCIDKDSGDVAALRGSRKFNILGTNTKVMNMEESNNGSLSAEFKHLTLRE
QRCGNGGRANCDASLIVTEELHLITETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWVWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNILVSPLIVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM

Linker: SGGGGSGGGGSGGGGSGGGGS

STAT5: MAGWIQAQQLGGDALRQMQVLYGQHFPIEVRHYLAQWIESQPWDAIDLDNPQDRAQATQLLEGLVQELQKAEHQVGEDGFLLKIKLGHYATQLQKTYD
RCPLEIVRCIRHILYNEQRLVREANNCSSPAGILVDAMSQKHLQINQTFEELRLVTQDTENELKKLQQTQEYFIIQYQESLRIQAQFAQLAQLSPQERLSRETAL
QQKQVSLEAWLQREAQTLQQYRVELAEKHQKTLQLLRKQQTIILDDELIQWKRRQQLAGNGGPPEGSLDVLQSWCEKLAEIIWQNRQQIRRAEHLCQQLPIPGPV
EEMLAEVNATITDIISALVTSTFIIEKQPPQVLKTQTKFAATVRLLVGGKLNVHMNPPQVKATIISEQQAKSLLKNENTRNECSGEILNNCCVMEYHQATGTLSA
HFRNMSLKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEV
QSNRGLTKENLVFLAQKLFNNSSSHLEDYSGLSVSWSQFNRENLPGWNYTFWQWFDGVMEVLKKHHKPHWNDGAILGFVNKQQAHDLLINKPDGTFLLRFSDSEI
GGITIAWKFDSPERNLWNLKPFTTRDFSIRSLADRLGDLSYLIYVFPDRPKDEVFSKYYTPVLAKAVDGYVKPQIKQVVPEFVNASADAGGSSATYMDQAPSPAV
CPQAPYNMYPQNPDHVLDQDGEFDLDETMDVARHVEELLRRPMDSLDSRLSPPAGLFTSARGSLS

Linker: EGRGSLLTCGDVEENPGP aCD19CAR: METDTLLLWVLLLWVPGSTGDIQMTQTTSSLSASLGDRVTISCRASQDISKYLNWYQQKPDGTVKLLIYHTSRLHSGVPSRFSGSGSGTDYSLTIS
NLEQEDIATYFCQQGNTLPYTFGGGTKLEITKAGGGGSGGGGSGGGGSEVKLQESGPGLVAPSQSLSVTCTVSGVSLPDYGVSWIRQPPRKGLEWLGVIW
GSETTYYNSALKSRLTIIKDNSKSQVFLKMNSLQTDDTAIYYCAKHYYYGGSYAMDYWGQGTSVTVSSDPTTPAPRPPTPAPTIASQPLSLRPEACRPAAGGAV
HTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGERRRGKGHDGLYQGLSTATKDTYDALHMQALPPR

Figure 10

SEQ ID NO: 10 (TIP - Linker - dZap70SH2 - linker - TEV - 2a - Truncated CD22 - CD19TM - Tyro-1 endodomain - Linker - TetRB - 2A - aCD19 - linker - TEV cleavage site x 3 - GOFSTAT5(S710F)

TIP: MWTWNAYAFAAP

Linker: SGGGS dZap70SH2domains: MPDPAAHLPFFYGSISRAEAEEHLKLAGMADGLFLLRQCLRSLGGYVLSLVHDVRFHHFPIERQLNGTYAIAGGKAHCGPAELCEFYSRDPDGLPCNLR
KPCNRPSGLEPQPGVFDCLRDAMVRDYVVRQTWKLEGEALEQAIISQAPQVEKLIATTAHERMPWYHSSLTREEAERKLYSGAQTDGKFLLRPRKEQGTYALSLIYGKTVYHYLISQ
DKAGKYCIPEGTKFDTLWQLVEYLKLKADGLIYCLKEACPNSSASNAGAAAPTLPAHPSTLTHP

Linker: SGGGGS

TEV: SLFKGPRDYNPISSTICHLTNESDGHTTSLYGIGFGPFIITNKHLFRRNNGTLLVQSLHGVFKVKNTTLQQHLIDGRDMIIIRMPKDFPPFPQKLKFREPQREERICLVTT
NFQTKSMSSMVSDTSCTFPSSDGIFWKHWIQTKDGQCGSPLVSTRDGFIVGIHSASNFTNTNNYFTSVPKNFMELLTNQEAQOWVSGWRLNADSVLWGGHKVFMSKPEEFFQPVKE
ATQLMNELVYSQ

2A: EGRGSLLTCGDVEENPGP

TruncatedCD22: MSRIDKSKVINSALELLNEVGIEGLITTRKLAQKLGVEQPTLYWHVKNKRALLDALAIEMLDRHITHFCPLEGESWQDFLRNNAKSFRCALLSHRDGAKVHLGTRPTEKQY
DAGSYSCWVNNSIGQTASKAWTLEVLYAPRRLRVSMSPGDQVMEGKSATLTCESDANPVSHYTWFDWNNQSLPYHSQKLRLEPVKVQHSGAYWCQGTNSVGKGRSPLSTLTVYYS
PETIGRR

CD19TM: AVTLAYLIFCLCSIVGILHL

Tyrp-1 endodomain: RARRSMDEANQPLLTDQYQCYAEEYEKLQNPNQSVV

Linker: GGSGGS

TETRb: MSRLDKSKVINSALELLNEVGIEGLITTRKLAQKLGVEQPTLYWHVKNKRALLDALAIEMLDRHITHFCPLEGESWQDFLRNNAKSFRCALLSHRDGAKVHLGTRPTEKQY
ETLENQLAFLCQQGFSLENALYALSAVGHFTLGCVLEDQEHQVAKEERETPTTDSMPPLLRQAIELFDHQGAEPAFLFGLELIICGLEKQLKCESGS

2A: EGRGSLLTCGDVEENPGP aCD19CAR: METDTLLLWVLLLWVPGSTGDIQMTQTTSSLSASLGDRVTISCRASQDISKYLNWYQQKPDGTVKLLIYHTSRLHSGVPSRFSGSGSGTDYSLTISNLEQEDIATYF
CQQGNTLPYTFGGGTKLEITKAGGGGSGGGGSGGGGSEVKLQESGPGLVAPSQSLSVTCTVSGVSLPDYGVSWIRQPPRKGLEWLGVIWGSETTYNSALKSRLTIIKDNS
KSQVFLKMNSLQTDDTAIYYCAKHYYYGGSYAMDYWGQGTSVTVSSDPTTTPAPRPPTPAPTIASQPLSLRPEACRPAAGGAV
HTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGREEYDVLDKRRG
RDPEMGGKPRRKNPQEGLYNELQKDKMAEAYSEIGMKGERRRGKGHDGLYQGLSTATKDTYDALHMQALPPR

Linker: GGSGGS

TEV cleavage site x3: ENLYFQGENLYFQGENLYFQG

GOF_STAT5(S710F): MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYD
RCPLELVRCIRHILYNEQRLVREANNCSSPAGILVDAMSQKHLQINQTFEELRLVTQDTENELKKLQOTQEYFIIQYQESLRIQAFQAQLAQLSPQERLSRETALQOKQVSLEAWL
QREAQTLQQYRVELAEKHQKTLQLLRKQQTIILDDELIQWKRRQQLAGNGGPPEGSLDVLQSWCEKLAEIIWQNRQQIRRAEHLCQQLPIPGPVEEMLAEVNATITDIISALVTST
FIIEKQPPQVLKTQTKFAATVRLLVGGKLNVHMNPPQVKATIISEQQAKSLLKNENTRNECSGEILNNCCVMEYHQATGTLSAHFRNMSLKRIKRADRRGAESVTEEKFTVLFESQ
FSVGSNELVFQVKTLSLPVVVIVHGSQDHNATATVLWDNAFAEPGRVPFAVPDKVLWPQLCEALNMKFKAEVQSNRGLTKENLVFLAQKLFNNSSHLEDYSGLSVSWSQFNRENL
PGWNYTFWQWFDGVMEVLKKHHKPHWNDGAILGFVNKQQAHDLLINKPDGTFLLRFSDSEIGITIAWKFDSPERNLWNLKPFTTRDFSIRSLADRLGDLSYLIYVFPDRPKDEVF
SKYYTPVLAKAVDGYVKPQIKQVVPEFVNAFADAGSSATYMDQAPSPAVCPQAPYNMYPQNPDHVLDQDGEFDLDETMDVARHVEELLRRPMDSLDSRLSPPAGLFTSARGSLS

Figure 11

SEQ ID NO: 11 (FRB – linker – STAT5 - 2a – FKBP12 – linker - STAT3)

FRB: ILWHEMWHEGLEEEASRLYFGERNVKGMFEVLEPLHAMMERGPQTLKETSFNQAYGRDLMEAQEWCRKYMKSGNVKDLLQAWDLYYHVFRRISK
Linker: SGGGGSGGGGSGGGGS
STAT5: MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYD
RCPLELVRCIRHILYNEQRLVREANNCSSPAGILVDAMSQKHLQINQTFEELRLVTQDTENELKKLQQTQEYFIIQYQESLRIQAFQAQLSPQERLSRETAL
QQKQVSLEAMLQREAQTLQQYRVELAEKHQKTLQLLRKQQTIILDDELIQWKRRQQLAGNGGPPEGSLDVLQSWCEKLAEIWQNRQQIRRAEHLCQQLPIPGPV
EEMLAEVNATITDIISALVTSTFIIEKQPPQVLKTQTKFAATVRLLVGGKLNVHMNPPQVKATIISEQQAKSLLKNENTRNECSGEILNNCCVMEYHQATGTLSA
HFRNMSLKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEV
QSNRGLTKENLVFLAQKLFNNSSSHLEDYSGLSVSWSQFNRENLPGWNYTFWQMFDGVMEVLKKHKPHWNDGAILGFVNKQQAHDLLINKPDGTFLLRFSDSEI
GGITIAWKFDSPERNLWNLKPFTTRDFSIRSLADRLGDLSYLIYVFPDRPKDEVFSKYYTPVLAKAVDGYVKPQIKQVVPEFVNASADAGGSSATYMDQAPSPAV
CPQAPYNMYPQNPDHVLDQDGEFDLDETMDVARHVEELLRRPMDSLDSRLSPPAGLFTSARGSLS
2A: EGRGSLLTCGDVEENPGP
FKBP12: GVQVETISPGDGRTFPKRGQTCVVHYTGMLEDGKKVDSSRDRNKPFKFMLGKQEVIRGWEEGVAQMSVGQRAKLTISPDYAYGATGHPGIIPPHATLV
FDVELLKLE
Linker: SGGGGSGGGGSGGGGS
STAT3: AQWNQLQQLQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQQGQANHPTAAVTEKQQMLEQHLQDVRKRVQDLEQKMKVVENLQDDFDFNYKTLKSQGDMQDLNGNNQSVTRQKMQQLEQ
MLTALDQMRRSIVSELAGLLSAMEYVQKTLTDEELADWKRRQQIACIGGPPNICLDRLENWITSLAESLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKFNILGTNTKVMNMEESNNGSLSAEFKHLTLRE
QRCGNGGRANCDASLIVTEELHLITFETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWWLDNIIDLVKKYIIALWNEGYIMGFISKERERAILSTKPPGTFLLRFSESSKEGGVTFTWVE
KDISGKTQIQSVEPYTKQQLNNMSFAEIIMGYKIMDATNILVSPLVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM

Figure 12

SEQ ID NO: 12 (TIP – linker - STAT5 – 2a – TetRB – linker - STAT3)

TIP: MWTWNAYAFAAP
Linker: SGGGGSGGGGSGGGGS
STAT5: MAGWIQAQQLQGDALRQMQVLYGQHFPIEVRHYLAQWIESQPWDAIDLDNPQDRAQATQLLEGLVQELQKKAEHQVGEDGFLLKIKLGHYATQLQKTYD
RCPLELVRCIRHILYNEQRLVREANNCSSPAGILVDAMSQKHLQINQTFEELRLVTQDTENELKKLQQTQEYFIIQYQESLRIQAQFAQLAQLSPQERLSRETAL
QQKQVSLEAWLQREAQTLQQYRVELAEKHQKTLQLLRKQQTIILDDELIQWKRRQQLAGNGPPEGSLDVLQSWCEKLAEIWQNRQQIRRAEHLCQQLPIPGPV
EEMLAEVNATITDIISALVTSTFIIEKQPPQVLKTQTKFAATVRLLVGGKLNVHMNPPQVKATIISEQQAKSLLKNENTRNECSGEILNNCCVMEYHQATGTLSA
HFRNMSLKRIKRADRRGAESVTEEKFTVLFESQFSVGSNELVFQVKTLSLPVVVIVHGSQDHNATATVLWDNAFAEPGRVPFAVPDKVLWPQLCEALNMKFKAEV
QSNRGLTKENLVFLAQKLFNNSSSHLEDYSGLSVSWSQFNRENLPGWNYTFWQMFDGVMEVLKKHHKPHWNDGAILGFVNKQQAHDLLINKPDGTFLLRFSDSEI
GGITIAWKFDSPERNLWNLKPFTTRDFSIRSLADRLGDLSYLIYVFPDRPKDEVFSKYYTPVLAKAVDGYVKPQIKQVVPEFVNASADAGGSSATYMDQAPSPAV
CPQAPYNMYPQNPDHVLDQDGEFDLDETMDVARHVEELLRRPMDSLDSRLSPPAGLFTSARGSLS
2A: EGRGSLLTCGDVEENPGP
TetRB: MSRLDKSKVINSALELLNEVGIEGLTTRKLAQKLGVEQPTLYWHVKNKRALLDALAIEMLDRHTHFCPLEGESWQDFLRNNAKSFRCALLSHRDGAKV
HLGTRPTEKQYETLENQLAFLCQQGFSLENALYALSAVGHFTLGCVLEDQEHQVAKEERETPTTDSMPPLLRQAIELFDHQGAEPAFLFGLELIICGLEKQLKCE
SGS
Linker: SGGGGSGGGGSGGGGS
STAT3: AQWNQLQQLDTRYLEQLHQLYSDSFPMELRQFLAPWIESQDWAYAASKESHATLVFHNLLGEIDQQYSRFLQESNVLYQHNLRRIKQFLQSRYLEKPME
IARIVARCLWEESRLLQTAATAAQGGQANHPTAAVVTEKQQMLEQHLQDVRKRVQDLEQKMKVVENLQDDFDFNYKTLKSQGDMQDLNGNNQSVTRQKMQQLEQ
MLTALDQMRRSIVSELAGLLSAMEYVQKTLTDEELADWKRRQQIACIGGPPNICLDRLENWITSLAESLQTRQQIKKLEELQQKVSYKGDPIVQHRPMLEERIV
ELFRNLMKSAFVVERQPCMPMHPDRPLVIKTGVQFTTKVRLLVKFPELNYQLKIKVCIDKDSGDVAALRGSRKFNILGTNTKVMNMEESNNGSLSAEFKHLTLRE
QRCGNGGRANCDASLIVTEELHLITFETEVYHQGLKIDLETHSLPVVVISNICQMPNAWASILWYNMLTNNPKNVNFFTKPPIGTWDQVAEVLSWQFSSTTKRGL
SIEQLTTLAEKLLGPGVNYSGCQITWAKFCKENMAGKGFSFWWLDNIIDLVKKYILALWNEGYIMGFISKERERAILSTKPPGTFLLRFSESSKEGGVTFTWVE
KDISGKTQIQSVEPYTKQQLNNMSFAEIIMGYKIMDATNILVSPLVYLYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPM (a)

CELL

CROSS-REFERENCE TO RELATED APPLICATIONS

This is a Divisional of U.S. application Ser. No. 16/646,906, filed Mar. 12, 2020, now U.S. Pat. No. 11,701,386, issued Jul. 18, 2023, which is a U.S. National Phase of International Application No. PCT/GB2018/052583, filed Sep. 12, 2018, which claims priority to Great Britain Application No. 1714718.2, filed Sep. 13, 2017.

INCORPORATION BY REFERENCE OF MATERIAL SUBMITTED ELECTRONICALLY

A Sequence Listing is incorporated herein by reference as part of the disclosure. The sequence listing was submitted as a text file named "53691A Seqlisting.XML", which was created on May 17, 2023 and is 24,720 bytes in size.

FIELD OF THE INVENTION

The present invention relates to a cell comprising a chimeric antigen receptor (CAR) and a constitutively active or inducible Signal Transducer and Activator of Transcription (STAT) molecule.

BACKGROUND TO THE INVENTION

Chimeric Antigen Receptors (Cars)

A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1).

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Car T Cell Engraftment and Proliferation

Function of CAR T cells depends on engraftment within the patients. In some settings, like ALL, engraftment of up to 9 months appears important to prevent relapse and effect sustained remissions. Present strategies to increase CAR T cell engraftment include generation of CAR T-cell product to result in naïve and central-memory T-cells, selection of co-stimulatory signals and/or co-administration of the CAR T cells with prolonged therapies (e.g., kinase inhibitors such as Ibrutinib). CAR T-cell persistence and activity can also be enhanced by administration of cytokines or by the CAR T-cells producing cytokines constitutively and by generating a CAR T cell product to result in a selection of co-stimulatory signals.

However, the above approaches have limitations. For example, prolonged exposure to chemotherapy may have undesirable short term and/or long-term side effects to the patient. In addition, systemic administration of cytokines can be toxic and constitutive production of cytokines may lead to uncontrolled proliferation and transformation (Nagarkatti et al (1994) PNAS 91:7638-7642; Hassuneh et al (1997) Blood 89:610-620).

There is therefore a need for methods for enhancing engraftment and expansion of T cells within a patient which are not associated with the disadvantages and problems mentioned above.

The typical format of a chimeric antigen receptor is shown. These are type I transmembrane proteins. An ectodomain recognizes antigen. This is composed of an antibody derived single-chain variable fragment (scFv) which is attached to a spacer domain. This in turn is connected to a transmembrane domain which acts to anchor the molecule in the membrane. Finally, this is connected to an endodomain which acts to transmits intracellular signals to the cell. This is composed of one or more signalling domains.

Figure 2:
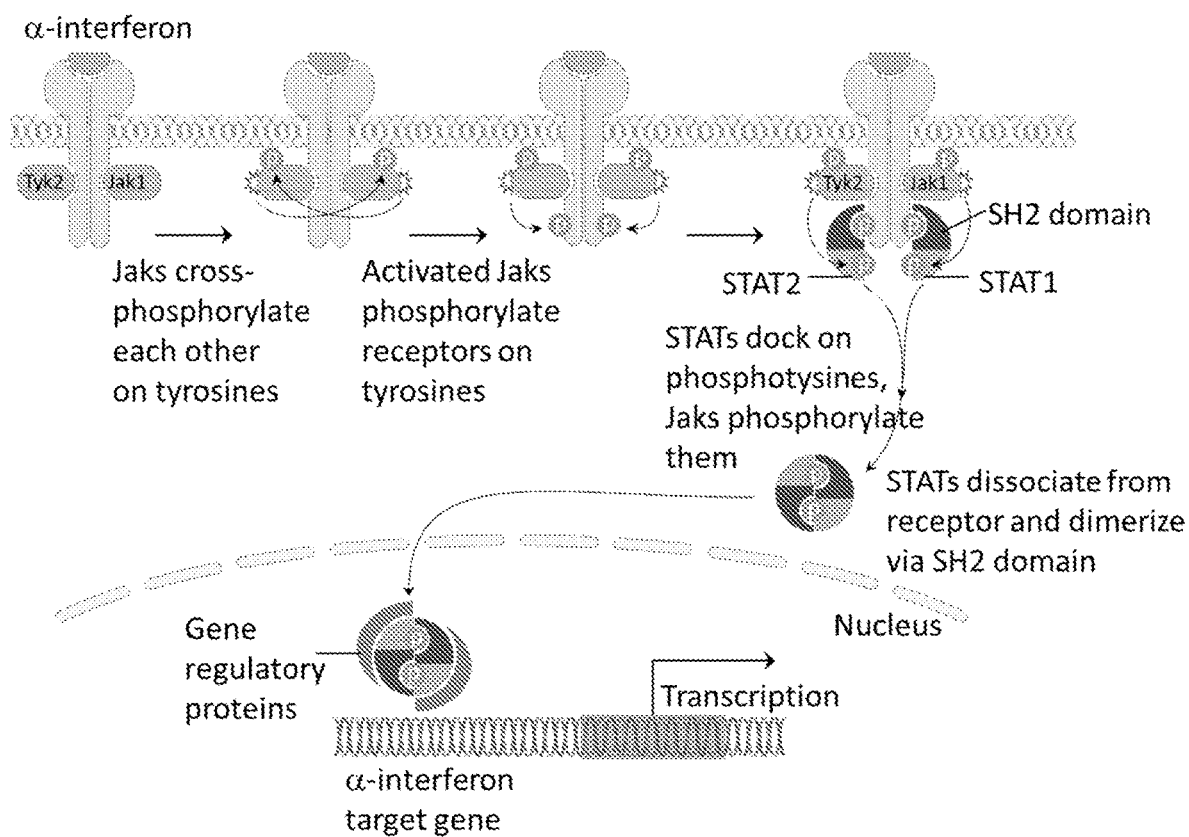

FIG. 2: Schematic diagram illustrating the JAK-STAT signaling pathway (activated by α-interferon).

Figure 3:
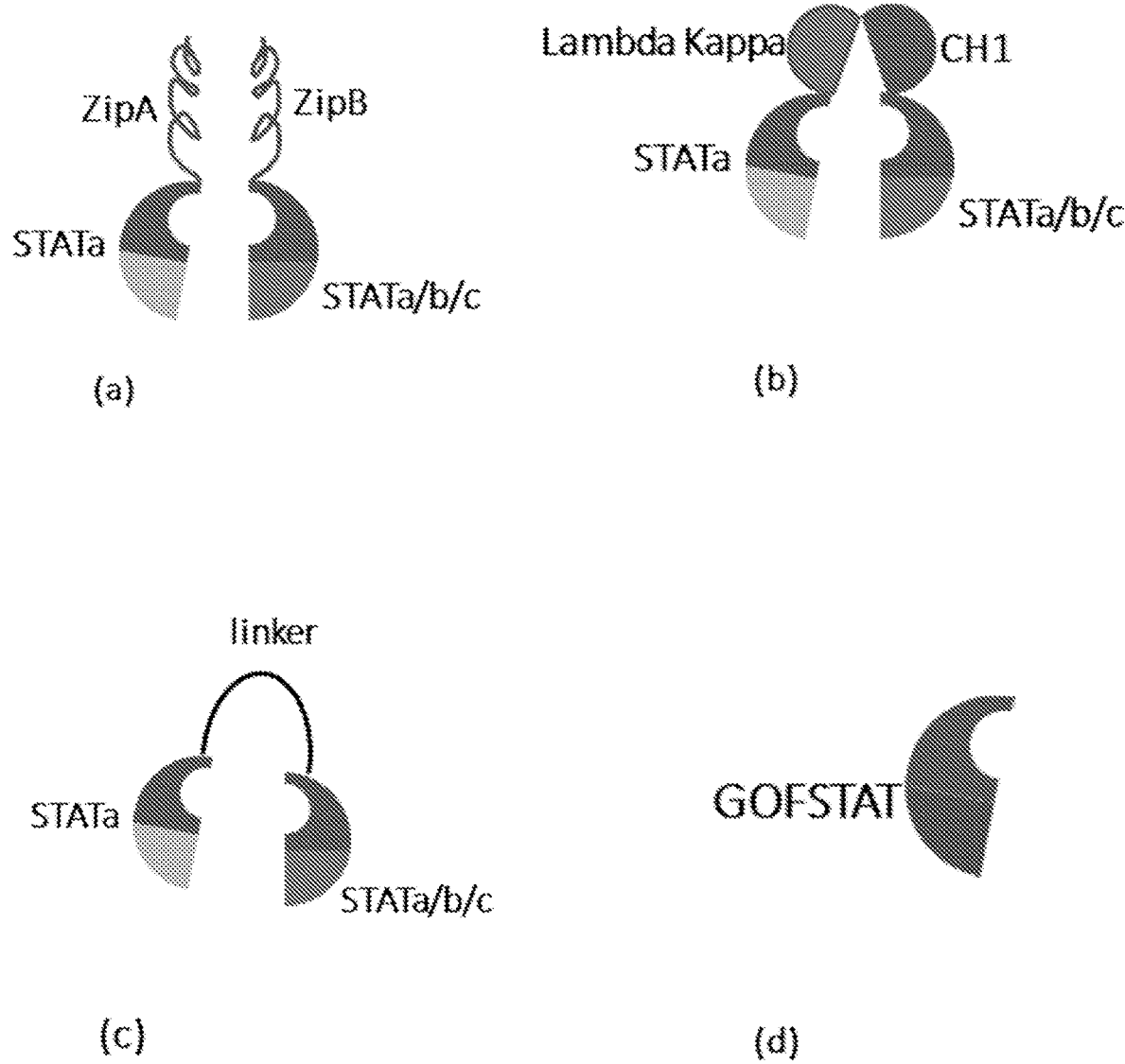

FIG. 3: Constitutively active STAT molecule structures

Various alternative arrangements are shown to produce a constitutively active STAT molecule. The structures shown in (a) and (b) are made up of two polypeptides, each having a dimerization domain. In the structure shown in (a), both polypeptides have leucine zipper dimerization domains. In the structure shown in (b), one polypeptide has an antibody-type heavy chain constant region and one polypeptide has as light chain constant region. The structure shown in (c) has a linker sequence permanently joining the two STAT polypeptides. The STAT molecule of (a) to (c) may be a heterozygous or homozygous STAT molecule, as indicated by STATa and STATa/b/c. In the structure shown as (d) the STAT molecule comprises a gain of function (GOF) mutation.

Figure 4:
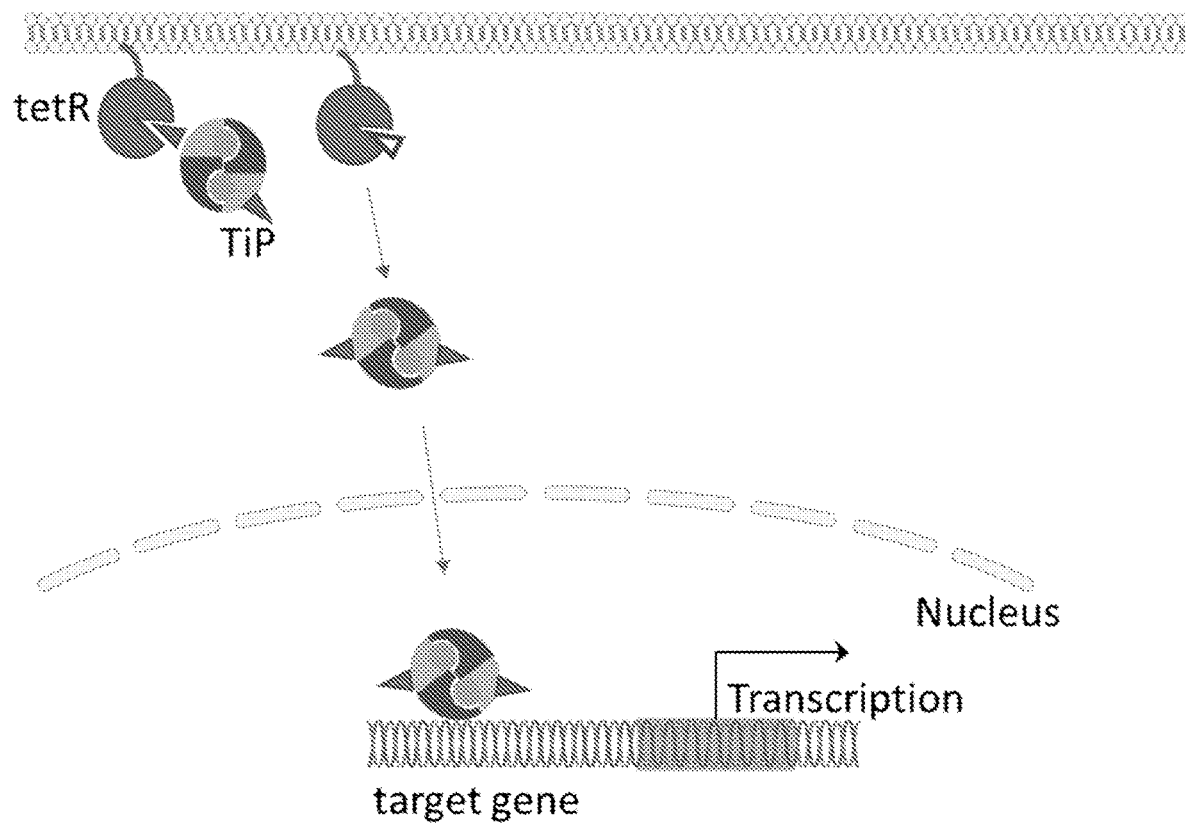

FIG. 4: Schematic diagram of a cell comprising a constitutively active STAT molecule which exerts its effect in the presence/absence of an agent. In this arrangement, the cell comprises a membrane-tethering molecule which has a first binding domain (BD) and a constitutively active STAT molecule which has a second BD. Proliferation/survival can be controlled by administration of an agent which disrupts binding of the first BD to the second BD, and leads to release of the active STAT molecule from the membrane-tethering molecule. Once released, the active STAT molecule is free to translocate to the nucleus, where it triggers DNA transcription.

Figure 5A:
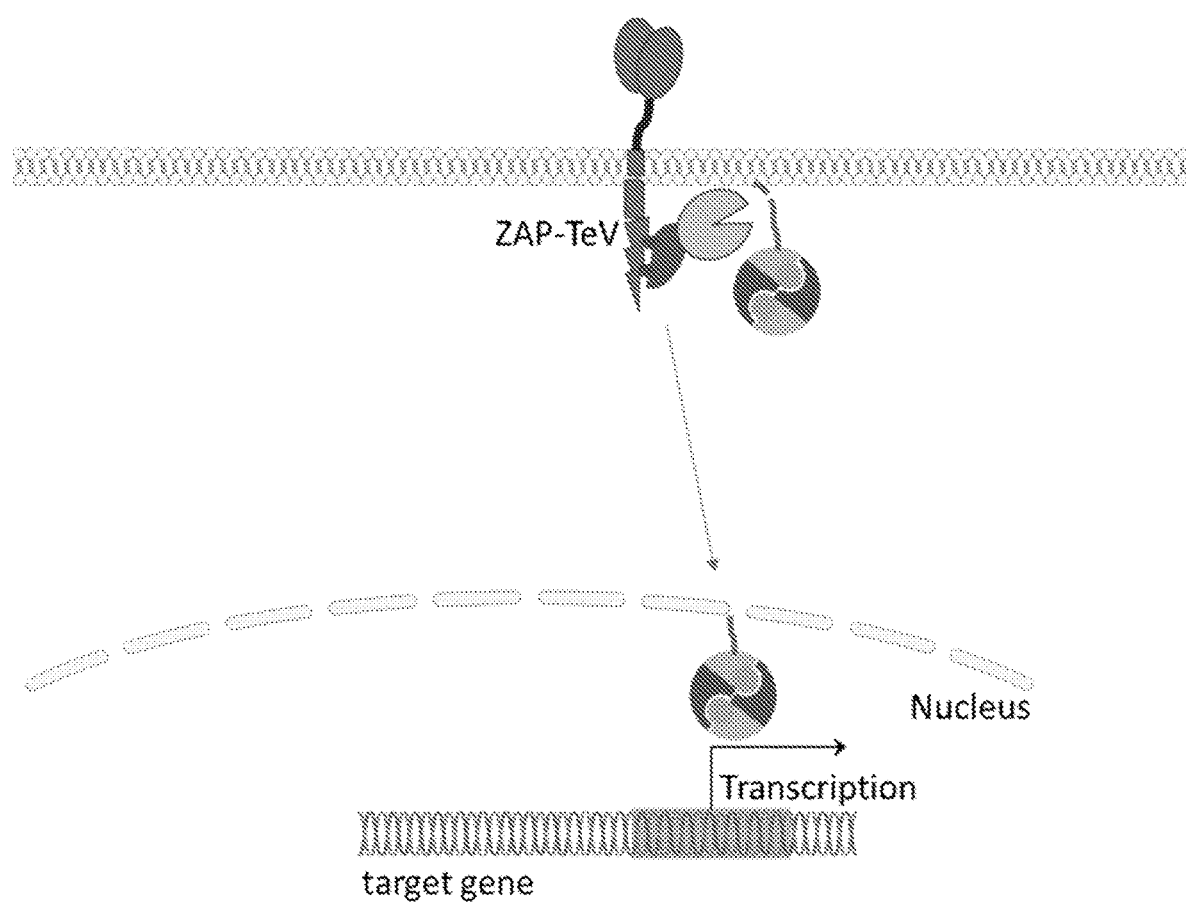
Figure 5B:
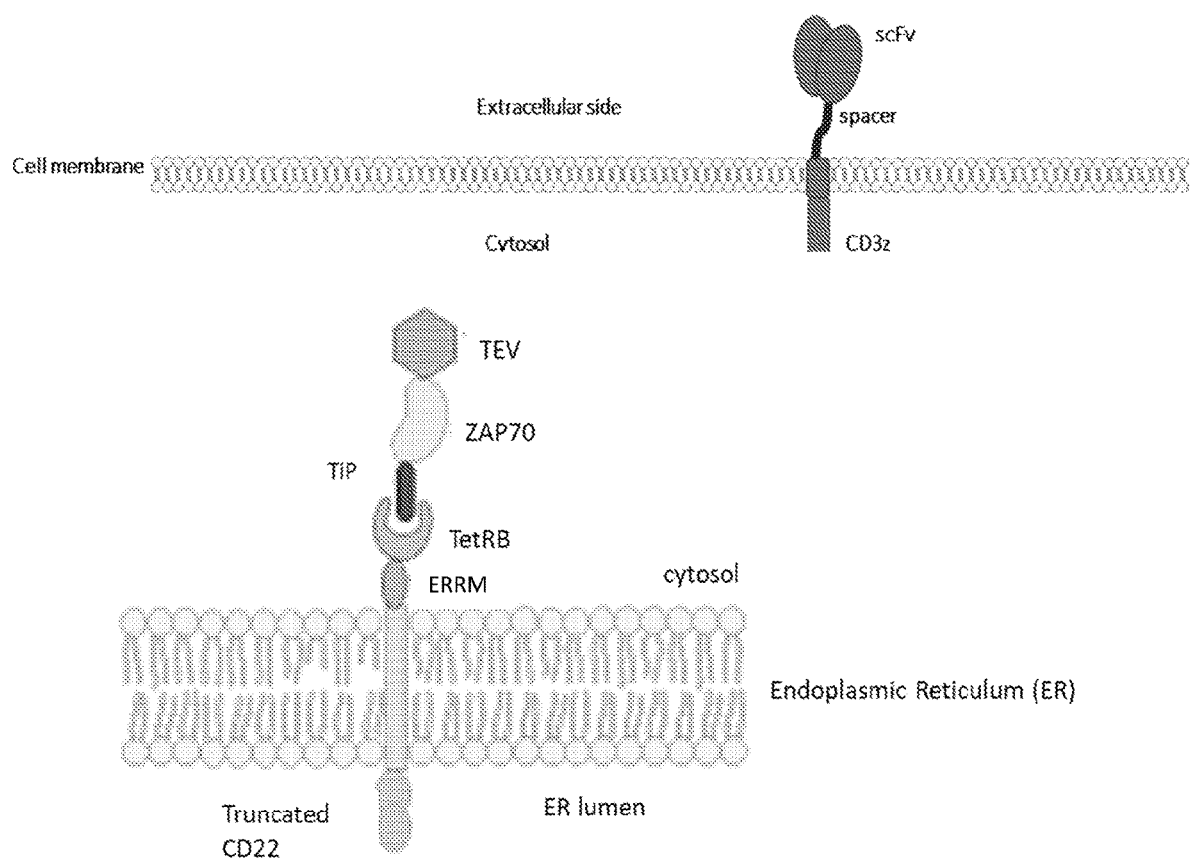

FIGS. 5(a) and 5(b): Schematic diagram of a cell comprising a constitutively active STAT molecule which is linked to recognition of a target antigen In the arrangement shown in (a) the cell comprises a chimeric molecule which comprises a CAR and a constitutively active STAT molecule. The chimeric molecule comprises a STAT release domain (e.g., protease cleavage site) between the STAT molecule and the CAR. The cell also comprises a STAT release molecule which releases the constitutively active STAT molecule by, for example, proteolytic cleavage.

In the arrangement shown in (a), the STAT release molecule comprises ZAP70 SH2 domains. When the CAR recognises its target antigen, the STAT release molecule binds phosphorylated immunoreceptor tyrosine based activation motifs (ITAMs) in the CAR endodomain. The protease domain of the STAT release molecule is then brought into proximity of the STAT release domain and the constitutively active STAT molecule is cleaved off. Once the constitutively active STAT molecule is released from the CAR, it can translocate to the nucleus and trigger DNA transcription.

In the arrangement shown in (b) the cell comprises a chimeric molecule which comprises a CAR linked to a constitutively active GOF STAT molecule by a STAT release domain having a protease cleavage site. The cell also comprises a STAT release molecule tethered to the endoplasmic reticulum (ER) via a retention motif. The STAT release molecule is released from the ER by addition of a small molecule. For example, in the arrangement shown, the STAT release molecule comprises TiP and the membrane tethering molecule comprises TetRB so that addition of tetracycline causes dissociation of the STAT release molecule. The STAT release molecule comprises a ZAP70 SH2 domain, so that when the CAR recognises its target antigen, the STAT release molecule binds to the phosphorylated ITAM of the CAR, and the constitutively active STAT is released from the CAR by cleavage at the protease cleavage site. Both (a) and (b) trigger DNA transcription by the activated STAT molecule only when the CAR recognises a target antigen. The latter provides added safety since proliferation/survival can be controlled by administration of an agent (in this case tetracycline).

Figure 6A:
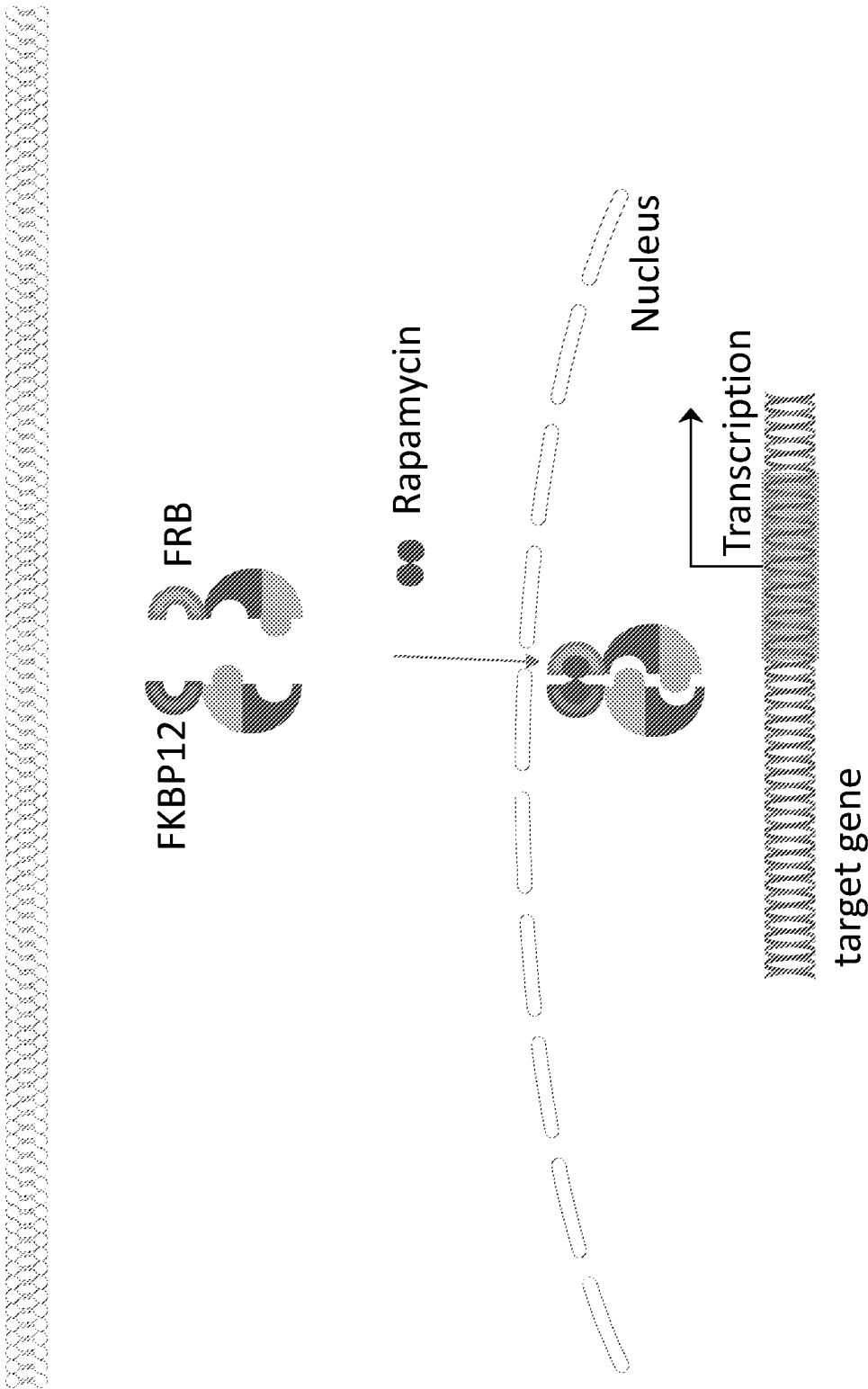
Figure 6B:
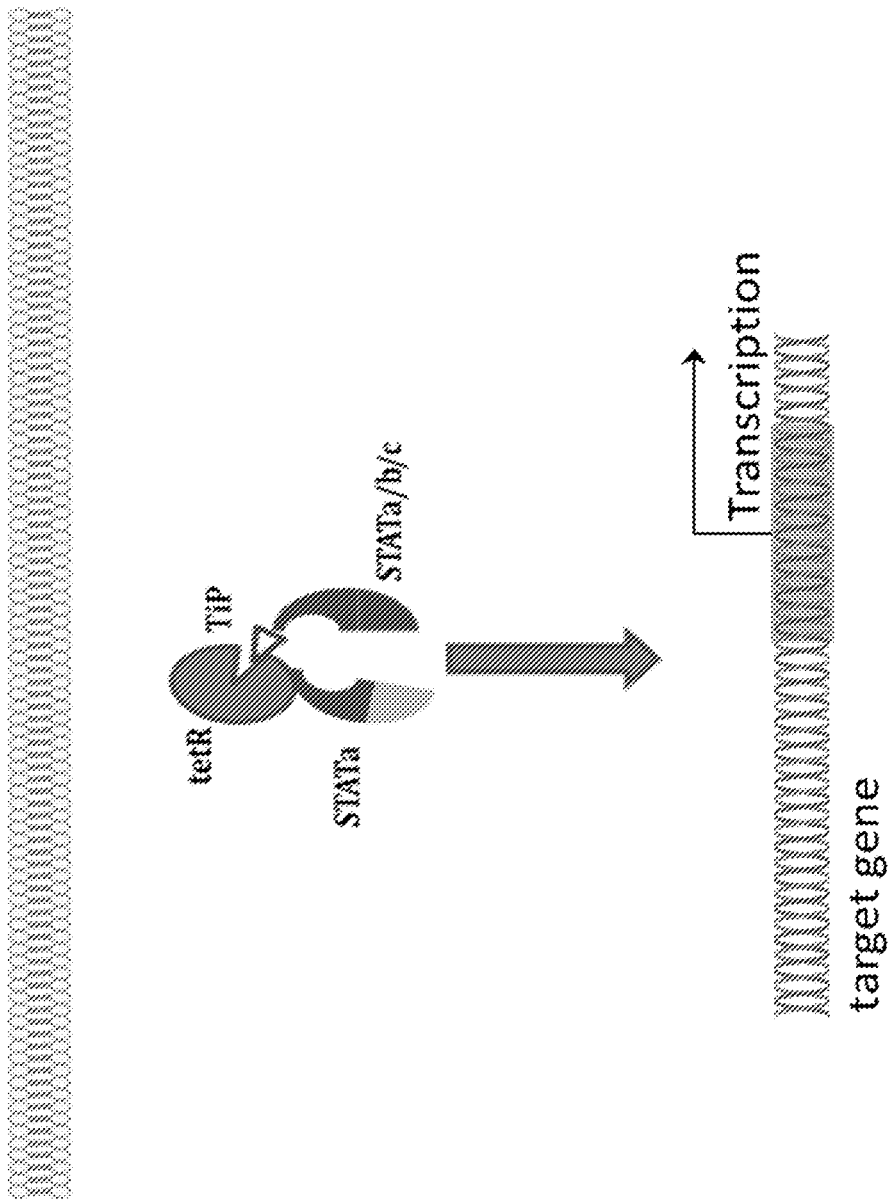

FIGS. 6(a) and 6(b): Schematic diagram of a cell comprising an inducible STAT molecule In the arrangement shown in (a), the cell comprises two STAT polypeptides with FKBP12/FRB hetrodimerization domains. Upon addition of an agent (rapamycin), dimerization of FKBP12 and FRB induces activation of the STAT molecule. In the arrangement shown in (b) the cell comprises an inducible STAT molecule which is inactivated in the presence of an agent. The cell of (b) comprises two STAT polypeptides, one with a TetR dimerization domain and one with a TiP dimerization domain. Addition of an agent such as tetracycline, doxycycline or minocycline causes dissociation of the STAT polypeptides.

FIG. 7: Amino acid sequence for a constitutively active STAT molecule of the type shown in FIG. 3c.

FIG. 8: Amino acid sequence for a construct which produces two proteins as illustrated in FIG. 4: a constitutively active STAT molecule with a TiP heterodimerisation domain; and a membrane tethering component having a myristoylation and palmitoylation sequence and a TetRB heterodimerisation domain.

FIG. 9: Amino acid sequence for a construct which produces three proteins as illustrated in FIG. 5a: a chimeric antigen receptor; a membrane-tethered molecule which comprises a Myristoylation and palmitoylation sequence a TEV cleavage site and a constitutively active STAT molecule; and an intracellular molecule which comprises ZAP70 SH2 domains, linked to the TEV protease.

FIG. 10: Amino acid sequence for a construct which produces three proteins as illustrated in FIG. 5b: a chimeric antigen receptor linked an intracellular constitutively active (GOF) STAT molecule by a TEV cleavage site; an intracellular molecule comprising TEV protease, Zap70 SH2 domains and a TiP heterodimerisation domain; and an ER-located protein which comprises truncated CD22 in the ER lumen, a CD19 transmembrane domain, a Tyro-1 endodomain and a TetRB heterodimerasation domain.

FIG. 11: Amino acid sequence for a construct which produces an inducible active STAT molecule as illustrated in FIG. 6a: a first polypeptide which comprises STAT5 and a FRB heterodimerisation domain; and a second polypeptide which comprises STAT 3 and an FKBP12 heterodimerisation domain.

FIG. 12: Amino acid sequence for a construct which produces an inducible active STAT molecule as illustrated in FIG. 6b: a first polypeptide which comprises STAT5 and an TiP heterodimerisation domain; and a second polypeptide which comprises STAT3 and an TetRB heterodimerisation domain.

Figure 13:
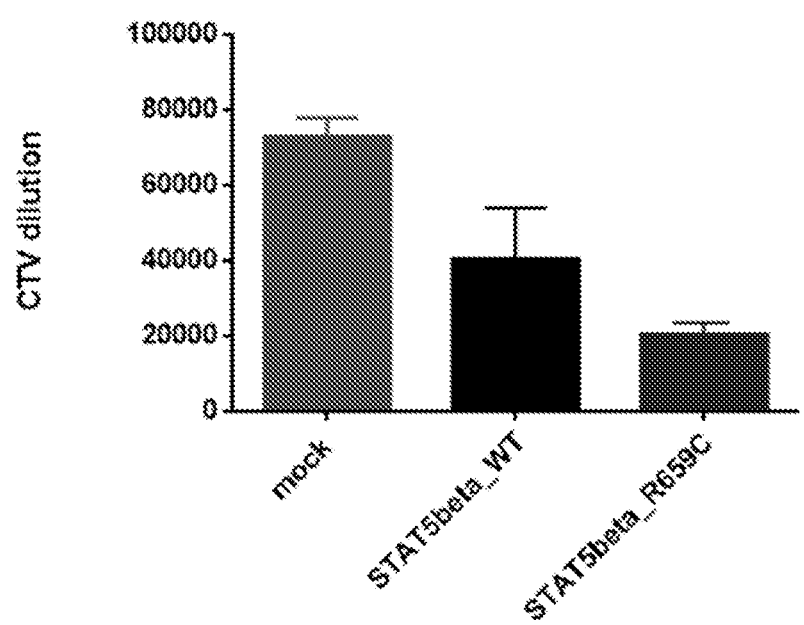

FIG. 13: Assessment of the propensity to proliferate in the absence of stimulation measured by CTV dilution. PBMCs transduced with either the wild type or mutant form of STAT5. They were labelled with cell trace violet (CTV) and left for 4 days in complete media without stimulation or exogenous cytokines. The constitutively active STAT molecule tested (STAT5beta R659C gain of function mutation) demonstrated decreased CTV dilution values compared to the wild type construct (STAT5beta_WT). These results show that the mutant construct has increased propensity to proliferate compared to the wild type construct.

Figure 14:
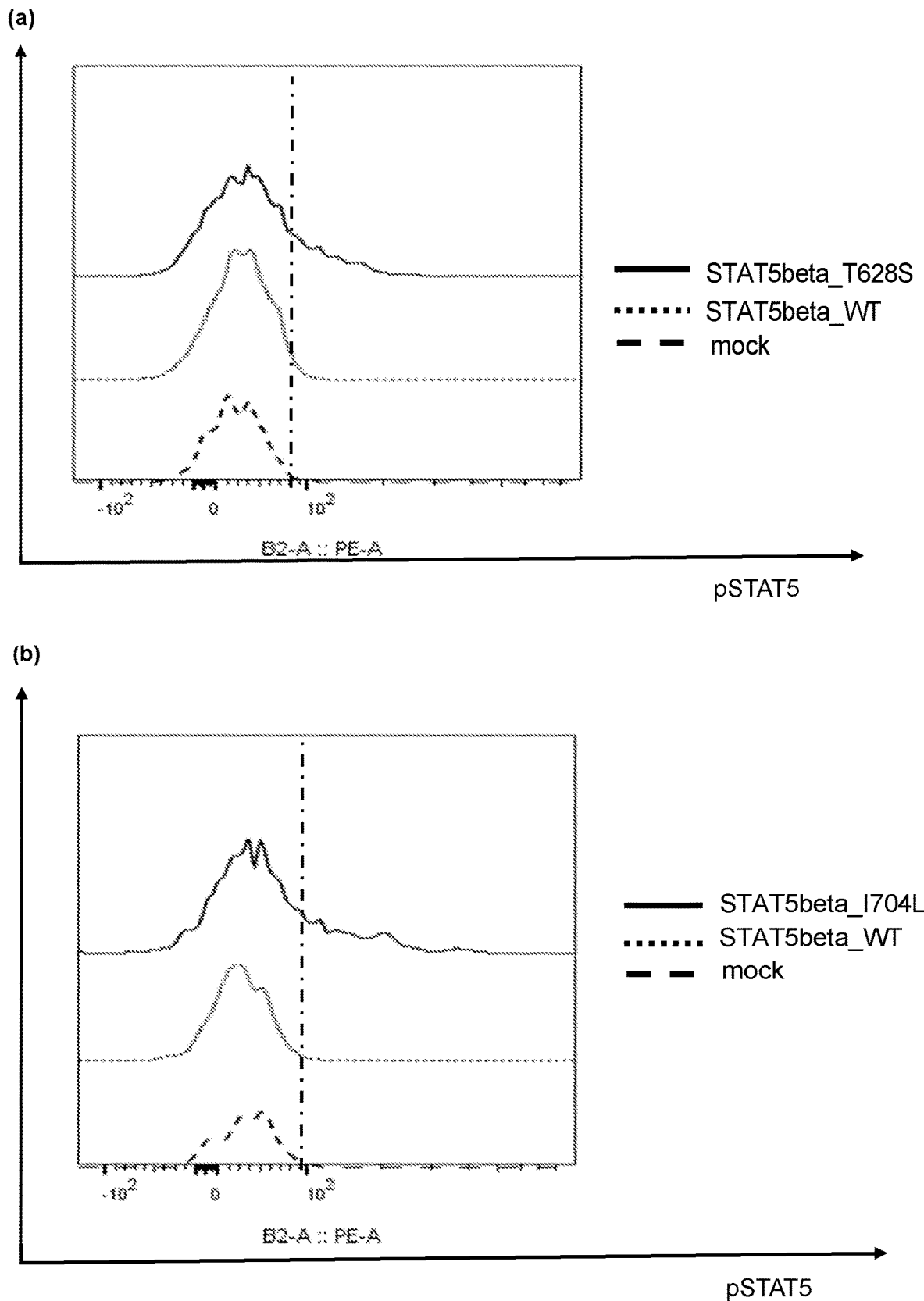

FIG. 14: Assessment of intracellular phosphorylated STAT5beta of constitutively active STAT mutants constructs compared to wild type. PBMCs transduced with either the wild type or mutant forms of STAT5 were left for 3 days in complete media without stimulation or exogenous cytokines. The baseline level of STAT phosphorylation was measured by flow cytometry. Both the constitutively active STAT molecules tested (a) STAT5beta T628S and (b) STAT5beta 1704F gain of function mutations showed a greater degree of STAT5 phosphorylation as indicated in the histograms of FIGS. 14 (a) and (b), respectively, compared to the wild type constructs or controls. This greater degree of STAT5 phosphorylation in the absence of stimulus indicates baseline activation of these mutants.

Figure 15:
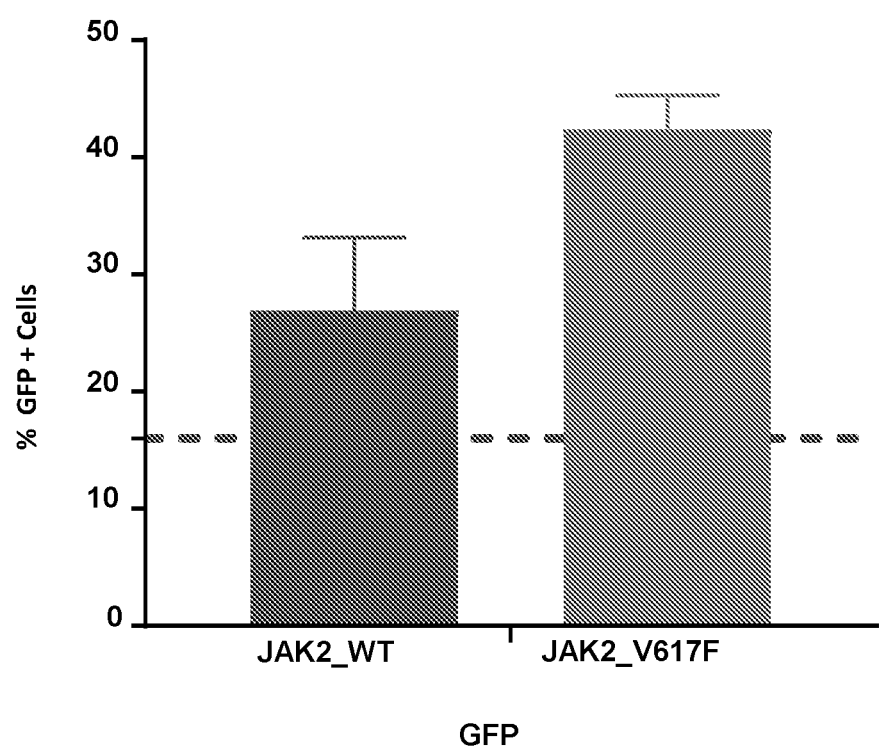
Figure 15:
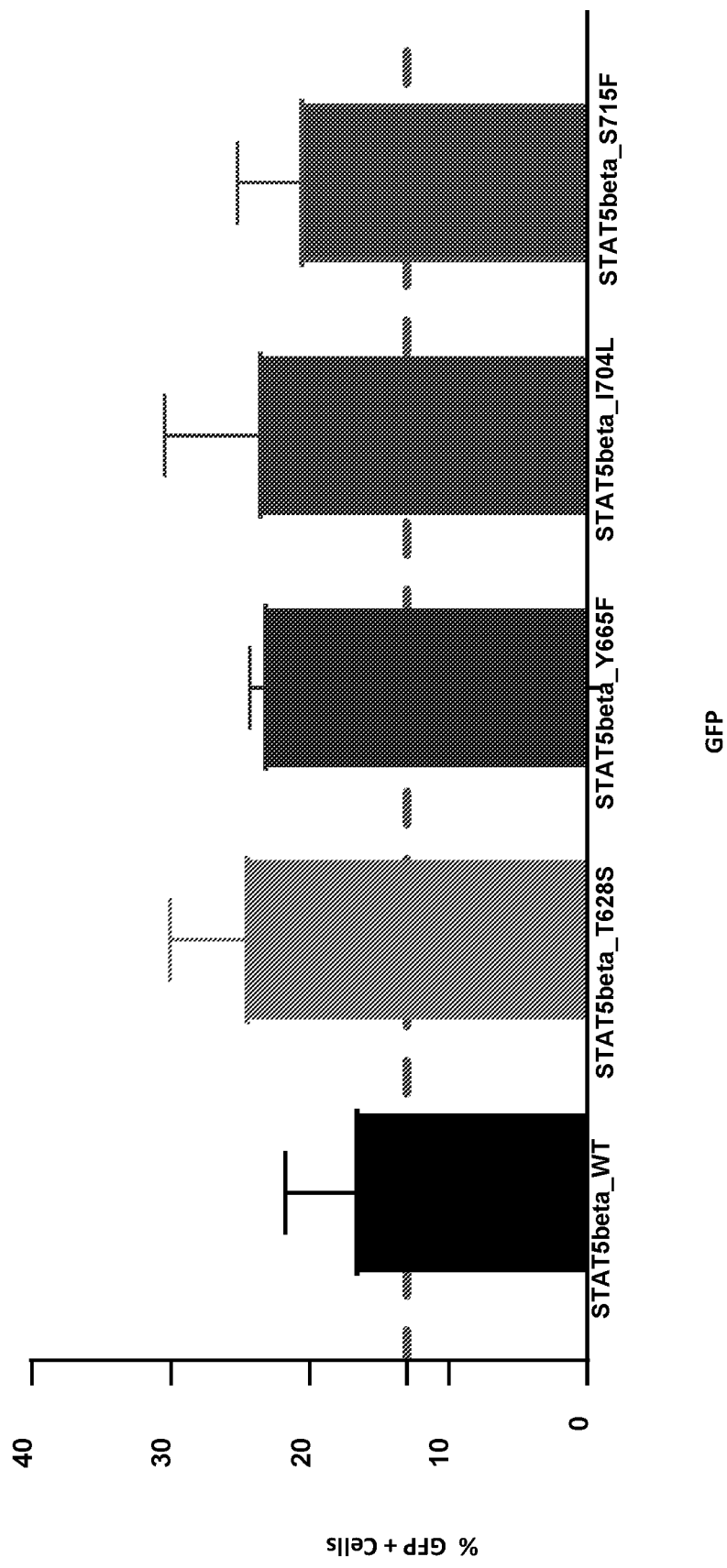

FIG. 15: Assessment of constitutively active JAK2 or STAT5 mutants to induce JAK2 or STAT5 dependent gene expression. A (a) JAK2 and (b) STAT5 dependent GFP reporter cell line was generated by transducing 293T cells with the self-inactivating vector construct comprising 3×STAT5 DNA responsive elements controlling the expression of GFP.

FIG. 15 shows an increase in GFP expression for the constitutively active (a) JAK2 V617F construct and (b) STAT5betaT628S, STAT5betaY665F, STAT5beta1704L, STATbetaS715F constructs, respectively, compared to the corresponding wild type constructs. This data indicates an increase in propensity for these mutants to drive genes from the STAT5 DNA responsive elements.

The dotted horizontal lines on the bar graphs of FIGS. 15(a) and 15(b) represents background expression.

SUMMARY OF ASPECTS OF THE INVENTION

The present inventors have found that it is possible to enhance engraftment and persistence of CAR-expressing cells, by including in the cell a constitutively active or inducible active Janus Kinase (JAK) or Signal Transducer and Activator of Transcription (STAT) molecule. These molecules are involved in the JAK STAT signalling cascade which triggers DNA transcription of cytokine-activated target genes.

In a first aspect, the present invention provides a cell which comprises a CAR and a constitutively active or an inducible Signal Transducer and Activator of Transcription (STAT) molecule.

The cell may be an immune effector cell, such as a T-cell or natural killer (NK) cell.

The STAT molecule of the cell may comprise a first STAT polypeptide comprising a first dimerizing domain (DD) and a second STAT polypeptide comprising a second DD, which specifically binds to the first DD.

The first and second DDs of the STAT molecule of the cell may comprise leucine zipper domains.

Alternatively, the first and second DDs of the STAT molecule of the cell may comprise a heavy chain constant region and a light chain constant region, respectively.

The STAT molecule of the cell of the present invention may be inducible. This means that the STAT molecule may be inducibly inactive or inducibly active.

The STAT molecule of the cell may be inducibly active in the presence of an agent which causes dimerization of the first DD and second DD of the STAT molecule, thereby inducing activation of the STAT molecule. The first DD may comprise FRB, the second DD may comprise FKBP12 and the agent may be rapamycin.

Alternatively, the STAT molecule of the cell may be inducibly inactive in the presence of an agent which causes dissociation of the first DD and second DD of the STAT molecule, thereby inducing non-activation of the STAT molecule. The first DD may comprise TetRB and the second DD may comprise TiP and the agent may be tetracycline, doxycycline or minocycline.

The STAT molecule of the cell of the present invention may be constitutively active.

A constitutively active STAT may comprise a Gain of Function (GOF) mutation.

Alternatively, a constitutively active STAT molecule of the cell may comprise a first STAT polypeptide and a second STAT polypeptide linked by a linker sequence.

The cell may comprise a membrane-tethering molecule comprising a tethering domain and a first binding domain (BD), and a constitutively active STAT molecule which comprises a second BD which binds specifically to the first BD. Binding of the first and second BD may be disrupted by the presence of an agent, such that in the presence of the agent the constitutively active STAT molecule dissociates from the membrane-tethering molecule, so that the constitutively active STAT molecule is free to translocate to the nucleus.

The first and second DD of the STAT molecule of the cell; or the first BD of the membrane-tethering molecule of the cell and second BD of the STAT molecule of the cell may comprise a Tet Repressor Protein (TetR) and a Transcription Inducing Peptide (TiP), respectively; and the agent may be tetracycline, doxycycline or minocycline.

The cell may comprise a) a CAR and a constitutively active STAT molecule joined by a STAT release domain and b) a STAT release molecule which releases the constitutively active STAT molecule from the CAR at the STAT release domain only upon recognition of a target antigen specific to the CAR, such that upon release, the constitutively active STAT molecule is free to translocate to the nucleus.

The STAT release molecule of the cell of the present invention may comprise a CAR targeting domain, for example which binds to a phosphorylated immunoreceptors tyrosine based activation motif (ITAM).

The CAR targeting domain of the cell of the present invention may comprise one or more ZAP70 SH2 domains.

The STAT release domain of the cell of the present invention may comprise a protease cleavage site, and the STAT release molecule of the cell may comprise a protease domain, such that upon recognition of a target antigen of the CAR, the protease domain cleaves at the protease cleavage site, releasing the STAT molecule.

The cleavage site may be a Tobacco Etch Virus (TEV) protease cleavage site.

In a second aspect, the present invention provides a cell which comprises a CAR and a constitutively active or an inducible Janus Kinase (JAK) molecule.

In a third aspect, the present invention provides a nucleotide sequence encoding a constitutively active STAT molecule or an inducible STAT molecule as defined in the first aspect of the invention.

In a fourth aspect, the present invention provides a nucleotide construct which comprises a first nucleotide sequence as defined in the third aspect of the invention, and a second nucleotide sequence encoding the CAR.

The nucleotide construct may further comprise a third nucleotide sequence encoding a membrane-tethering molecule as defined in the first aspect of the invention.

The nucleotide construct may comprise a first nucleotide sequence encoding a CAR and a constitutively active STAT molecule joined by a STAT release domain as defined in a first aspect of the invention, and a second nucleotide sequence encoding for a STAT release molecule, as defined in a first aspect of the invention.

In a fifth aspect, the present invention provides a vector comprising a nucleotide sequence according to the third aspect or a nucleotide construct as defined in the fourth aspect.

In a sixth aspect, the present invention provides a pharmaceutical composition comprising a plurality of cells according to the first and/or second aspect of the invention.

In a seventh aspect, the present invention provides a pharmaceutical composition according the sixth aspect of the invention for use in treating and/or preventing a disease.

In an eighth aspect, the present invention provides a method for treating and/or preventing a disease, which comprises the step of administering a pharmaceutical composition according to the fifth aspect of the invention to a subject.

The method may comprise the following steps:
 (i) isolation of a cell containing sample;
 (ii) transduction or transfection of the cells with a nucleotide sequence according to the third aspect, a nucleotide construct according to a fourth aspect, or a vector according to the fifth aspect of the invention; and
 (iii) administering the cells from (ii) to a subject.

The method may involve monitoring the progression of disease and/or monitoring toxic activity in the subject and may comprise the step of administering an agent for use in the cell as defined the first aspect, to the subject to provide acceptable levels of disease progression and/or toxic activity.

In a ninth aspect, the present invention provides a use of a pharmaceutical composition according to sixth aspect of the invention in the manufacture of a medicament for the treatment and/or prevention of a disease.

The disease may be cancer.

T cells, as well as CAR T cells, require cytokines to proliferate and survive. The present invention effectively hijacks the cytokine-activated JAK/STAT intracellular signalling cascade to enhance engraftment of CAR T cell in a patient. The incorporation of a constitutively active or inducible STAT molecule into a cell increases the transmission of information from chemical signals to the nucleus, resulting in increased expression of cytokine-activated target genes, and thereby increases persistence and cell survival of the CAR T cell.

DETAILED DESCRIPTION

Chimeric Antigen Receptors (Cars)

Figure 1:
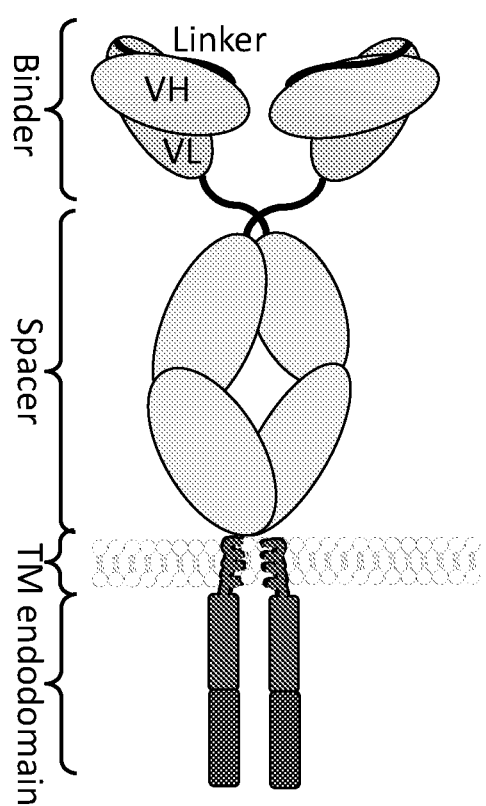
FIG. 1—Standard design of a Chimeric Antigen Receptor

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A spacer domain may be necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the 35 intracellular part of a T-cell co-stimulatory molecule to that of CD3 results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41 BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus, the CAR directs the specificity and cytotoxicity of the T cell towards cells expressing the targeted antigen.

In the first aspect, the present invention relates to a cell which comprises a Chimeric Antigen Receptor (CAR) and a constitutively active or inducible Signal Transduction and Activator of Transcription (STAT) molecule.

The STAT molecule is part of the JAK STAT signalling pathway which plays a role in cytokine-activated immune responses.

Jak/Stat Signalling Pathway

Cytokines are regulatory molecules that coordinate immune responses. The most typical cytokine receptor is a protein that forms a stable association with a cytoplasmic tyrosine kinase known as the cytokine-activated Janus Kinase (JAK). This type of signaling is a rapid way to turn on a set of genes via triggering Signal Transducer and Activator of Transcription (STAT) molecules.

The JAK-STAT signalling pathway consists of three main components: (1) a receptor which penetrates the cell membrane (2) Janus kinase (JAK), which is bound to the receptor and (3) Signal Transducer and Activator of Transcription (STAT), which carries the signal into the nucleus and DNA. FIG. 2 is a schematic diagram illustrating an α-interferon activated JAK STAT pathway, which activates the α-interferon target gene.

JAK

JAK is a family of intracellular tyrosine kinases that transduce cytokine-mediated signals. JAKs possess two phosphate-transferring domains, one exhibiting kinase activity and the other negatively regulating the kinase activity of the first.

There are four JAK family members: Janus Kinase 1 (JAK1); Janus Kinase 2 (JAK2); Janus Kinase 3 (JAK3); Tyrosine Kinase 2 (TYK2). Somatic activating mutations in JAK1, JAK2, and JAK3 have been identified in paediatric acute lymphoblastic leukemia (ALL) e.g., JAK2 mutations have been detected around the pseudokinase domain R683G in Down syndrome childhood B-ALL.

JAKs range from 120-140 kDa in size and have seven defined regions of homology (JH1-7). At the C-terminal end, JH-1 is the kinase domain important for the enzymatic activity of JAK and contains typical features of a tyrosine kinase such as conserved tyrosine resides (Y1038/Y1039 in JAK1, Y1007/Y1008 in JAK2, Y980/Y981 in JAK3 and Y1054/Y1055 in TYK2). Phosphorylation of these dual tyrosine residues leads to the conformations changes in JAK to facilitate binding of substrate. JH2 is a pseudokinase, structurally similar to JH1 but lacking enzymatic activity. This domain rather regulates the activity of JH1. The JH-3 and JH-4 domains of JAKs share homology with Src homology 2 (SH2) domains.

The tyrosine kinase activity of JAK is activated when the regulatory molecule binds and brings two receptor molecules together to form a dimer. Dimerization brings the two JAKs into close proximity, where they can phosphorylate each other. Phosphorylation further activates JAK, allowing it to phosphorylate the receptor. The phosphotryosine SH2 domains on the receptor proteins are binding sites for STAT proteins.

The binding of various ligands, usually cytokines such as interferon, interleukin and growth factors to cell surface receptors, activate associated JAKs, increasing their kinase activity, which then in turn activates STAT, triggering transcriptional activation of a cytokine-activated gene of interest.

In the context of the present invention, a constitutively active JAK molecule may be made by expressing two JAK polypeptides which spontaneously dimerise or are linked by a linker, as described below for constitutively active STAT molecules. Alternatively, constitutively active JAK may be expressed which comprises a gain-of-function mutation.

An inducible active JAK molecule may be by expressing two JAK polypeptides which dimerise in the presence of absence of an agent, as described below for STAT.

Signal Transducer and Activator of Transcription (Stat)

Signal Transducer and Activator of Transcription (STAT) molecules are a family of transcription factors that are involved in cytokine-mediated signal transduction. STAT transcription factors are recruited to the cytoplasmic region of cell surface receptors and are activated via phosphorylation. Once activated, they dimerize to form an activated STAT molecule comprising a first polypeptide and a second polypeptide, and translocate into the cell nucleus where they influence gene expression. They play a role in regulating cell growth processes and cell differentiation.

Each first and second polypeptide of the STAT molecules possess SH2 domains capable of binding phosphotyrosine residues recruited to the receptors, and are themselves tyrosine-phosphorylated by JAKs. These phosphotyrosines then act as binding sites for SH2 domains of other STAT molecules, mediating the dimerization.

Dimerization of the first and second polypeptide of the STAT molecule may be hetero- or homodimerization, for example, represented in FIGS. 3(a)-(d), STATa with STATa is homodimerization whereas STATa with either STATb or STATc is heterodimerization. Activated STAT dimers accumulate in the cell nucleus and activate transcription of their target genes.

There are seven mammalian STAT family members that have been identified: STAT1, STAT2, STAT3, STAT4, STAT5A, STAT5B and STATE. All seven STAT proteins share a common structural motif consisting of an N-terminal domain followed by a coiled-coil, DNA-binding, linker, Src homology 2 (SH2), and a C-terminal transactivation domain. Both the N-terminal and SH2 domains mediate homo or heterodimer formation, while the coiled-coil domain functions partially as a nuclear localization signal (NLS). Transcriptional activity and DNA association are determined by the transactivation and DNA-binding domains, respectively.

The presence of different STAT molecules in cells and activation of different cytokine receptors will result in the formation of different STAT dimers. Each naturally occurring STAT molecule is a dimer and binds to a specific DNA sequence found in the promoters of certain genes. Each cytokine activates a specific set of genes to cause a specific response in the cell. For example the STAT3/STAT1 polypeptide dimer is activated by the gp130 CD receptor and the STAT5/STAT3 polypeptide dimer is activated by the IL-2Rβ ICD.

Constitutively Active Stat Molecule

STAT molecules are considered latent transcription factors, meaning that they are always present, and waiting to be activated. A constitutively active STAT molecule triggers signal transduction without the dependency of the intracellular cytokine level or the phosphorylation state of various upstream signalling molecules in the JAK STAT signalling cascade. Co-expressing a constitutively active STAT with a CAR increases the proximity of the STAT molecule to the CAR compared to the physiological level of STAT freely circulating in the cytosol of the cell. The constitutively active STAT molecule in particular is advantageous as it may also bypass the usual requirement to activate JAK upstream of STAT activation.

The present inventors propose a number of different mechanisms to activate DNA transcription of the cytokine-activated target gene via STAT activation. The STAT molecule may be engineered to be constitutively active demonstrated schematically in FIGS. 3(a), (b), (c) and (d). For example, FIGS. 3(a) and (b) comprise a first and second polypeptide that are engineered to be physically bound together via the first and second dimerization domain (DD), without the need for a separate molecule acting as an "inducer" of dimerization.

First and Second Dimerisation Domain (DD)

The cell of the present invention may be engineered such that it comprises a STAT molecule, wherein the STAT molecule comprises a first STAT polypeptide comprising a first dimerizing domain (DD) and a second STAT polypeptide comprising a second DD, and wherein the first and second DD specifically bind to each other. In one embodiment, the dimerization of the first and second dimers occurs spontaneously, in which case the STAT protein will be constitutively active.

A large variety of appropriate dimerization domains are known in the art, examples of which are provided herein.

Leucine Zipper Domain

The first and second dimerization domains may be leucine zippers (FIG. 3(a)).

A leucine zipper is a super-secondary structure that functions as a dimerization domain. Its presence generates adhesion forces in parallel alpha helices. A single leucine zipper consists of multiple leucine residues at approximately 7-residue intervals, which forms an amphipathic alpha helix with a hydrophobic region running along one side. This hydrophobic region provides an area for dimerization, allowing the motifs to "zip" together. Leucine zippers are typically 20 to 40 amino acids in length, for example approximately 30 amino acids.

The first and/or second dimerization domain may comprise the sequence shown as SEQ ID NO: 1 or 2. The first dimerization domain may comprise the sequence shown as SEQ ID NO: 1 and the second dimerization domain may comprise the sequence shown as SEQ ID NO: 2, or vice versa.

```
SEQ ID NO: 1:
QLEKELQALEKENAQLEWELQALEKELAQ

SEQ ID NO: 2:
QLEKKLQALKKKNAQLKWKLQALKKKLAQ
```

In certain embodiments, the first and second dimerization domains may be acidic (e.g. SEQ ID NO: 1) or basic (e.g. SEQ ID NO: 2) leucine zippers. In particular, where the first heterodimerization domain is an acidic leucine zipper, the second heterodimerization is a basic leucine zipper and vice versa.

Heavy Chain and Light Chain Constant Region

Dimerisation of the first and second STAT polypeptides may be based on the dimerization domain of an antibody. In this arrangement the STAT polypeptides comprise the dimerization portion of a heavy chain constant domain (CH) and a light chain constant domain (CL) as depicted in FIG. 3(b). The dimerization portion of a constant domain is the part of the sequence which forms the inter-chain disulphide bond.

Linker Regions

Alternatively, the first and second polypeptides of STAT molecule may be linked together via a linker sequence (FIG. 3(c)). An example of an appropriate linker sequence could be the Glycine Serine linker sequence:

```
SEQ ID NO: 3:
GGSG

SEQ ID NO: 4:
GSGSGS

SEQ ID NO: 5:
GGSGGGSG

SEQ ID NO: 6:
SGGSGGSGG
```

Gain of Function (GOF) Mutation

A Gain Of Function (or GOF) mutation is a type of mutation in which the altered gene to product possesses a new molecular function or a new pattern of gene expression (FIG. 3(d)). This new molecule function may be activation.

A specifically engineered GOF of a STAT molecule may be a constitutively active STAT molecule of the cell. Here, the site of the mutation is engineered at a particular residue of the STAT molecule responsible for the conformational change that occurs when the STAT molecule activates. This allows for activation without dimerization of the first and second polypeptide of a STAT dimer molecule since the mutation itself activates the STAT molecule.

A well-known example of a GOF mutation is of the STAT3 gene. This results in a condition (known as STAT3 GOF disease) wherein the STAT3 gene is hyperactive, leading to intrinsic increase of transcriptional activity and over-active T cell activity (Milner et al., Blood 2015 125: 591-599). The mutation comprises various mutations in multiple domains of the protein including the DNA binding, SH2 and C-terminal transactivation domains.

An example of a GOF mutation is S710F for STAT5, as shown in the sequence given in FIG. 10.

Inducible Stat Molecule

Alternatively, the STAT molecule may be inducible, and can be triggered to be active or inactive by, for example, addition of a small molecule such as an agent. This embodiment provides a means of controlling the activation or inactivation of a STAT molecule, in response to, for example, monitoring the progress of CAR T cell engraftment in the patient.

Agent

Dimerization of the first and second DDs of the first and second polypeptides of the inducible STAT molecule may occur only in the presence of an agent, such as with a chemical inducer of dimerization (CID). In bringing the two DDs together, the first and second polypeptides of the STAT dimer are brought together causing activation of the STAT molecule.

Alternatively, the agent may cause chemical dissociation of dimerization (CDD) of the first and second DDs by competitively binding to one of the DDs, and thus inhibiting dimerization of the first and second DDs, and therefore separating the first and second polypeptides of the STAT dimer. The CDD therefore prevents activation of the STAT molecule.

Suitable DDs and their associated agents are described in WO2015/150771, the contents of which are hereby incorporated by reference.

For example, one dimerization domain may comprise the rapamycin binding domain of FK-binding protein 12 (FKBP12), the other may comprise the FKBP12-Rapamycin Binding (FRB) domain of mTOR; and the CID agent may be rapamycin or a derivative thereof. In this embodiment, the STAT molecule is activated with addition of the agent Rapamycin since it induces dimerization of the first and second dimerization domains of the STAT molecule (see FIG. 6(a)).

One dimerization domain may comprise the FK506 (Tacrolimus) binding domain of FK-binding protein 12 (FKBP12) and the other dimerization domain may comprise the cyclosporin binding domain of cylcophilin A; and the CID may be an FK506/cyclosporin fusion or a derivative thereof.

One dimerization domain may comprise an oestrogen-binding domain (EBD) and the other dimerization domain may comprise a streptavidin binding domain; and the CID may be an estrone/biotin fusion protein or a derivative thereof.

One dimerization domain may comprise a glucocorticoid-binding domain (GBD) and the other dimerization domain may comprise a dihydrofolate reductase (DHFR) binding domain; and the CID may be a dexamethasone/methotrexate fusion protein or a derivative thereof.

One dimerization domain may comprise an O6-alkylguanine-DNA alkyltransferase (AGT) binding domain and the other dimerization domain may comprise a dihydrofolate reductase (DHFR) binding domain; and the CID may be an O6-benzylguanine derivative/methotrexate fusion protein or a derivative thereof.

One dimerization domain may comprise a retinoic acid receptor domain and the other dimerization domain may comprise an ecodysone receptor domain; and the CID may be RSL1 or a derivative thereof.

Alternatively, one dimerization domain may comprise Tet Repressor Protein (TetR) and the other dimerization domain may comprise a Transcription Inducing Peptide (TiP); and the CDD agent may be tetracycline, doxycycline or minocycline or a derivative thereof.

Membrane Tethering Molecule and Tethering Domain

In one embodiment, the cell of the invention comprising a CAR and a constitutively active STAT molecule, further comprises a membrane tethering molecule comprising a tethering domain and a first binding domain (BD). The constitutively active STAT molecule comprises a second BD, which binds specifically to the first BD.

The membrane tethering molecule may tether the first BD to the plasma membrane, as shown in FIG. 4. Alternatively, the membrane tethering molecule may tether the first BD to an endoplasmic reticulum (ER) membrane. The membrane tethering molecule may comprise an ER retention motif (ERRM) as shown in FIG. 5(b). A possible ERRM may comprise the Tyrp-1 endo peptide sequence.

First and Second Binding Domain (BD)

As with the first and second DD, the first and second BD of the invention may be a Tet Repressor Protein (TetR) and a Transcription Inducing Peptide (TiP), respectively; and the agent may be tetracycline, doxycycline or minocycline.

Addition of a CDD agent such as tetracycline causes dissociation of the first BD (e.g., TetR) and second BD (e.g., TiP), such that the constitutively active STAT molecule is released from being tethered to the membrane (plasma or ER), freeing the molecule to translocate to the nucleus and trigger DNA transcription of the target gene. Tetracycline competitively binds to TeTR, displacing TiP from the membrane loci, so that the STAT molecule it is free to translocate through the cytosol to the nucleus.

Stat Release Molecule and Stat Release Domain

The STAT release molecule comprises a domain capable of cleaving the site between the CAR and the active STAT molecule.

The STAT release domain may comprise any sequence which enables the CAR and the STAT molecule of the cell of the invention to become separated, permitting the STAT molecule to be released and then translocate to the nucleus. The STAT release domain may comprise a cleavage site.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

Stat Molecule Linked to Car Target Antigen Recognition

In one embodiment, the STAT release domain is only cleaved by the STAT release molecule upon recognition of a target antigen by the CAR.

The STAT release molecule may comprise a CAR targeting domain which binds to a phosphorylated immunoreceptors tyrosine based activation motif (ITAM) on the CAR endodomain. The CAR targeting domain may comprise ZAP70 SH2 domains, as shown in FIGS. 5(a) and 5(b).

Antigen Binding Domain

The antigen-binding domain is the portion of the CAR which recognises the target antigen. It usually comprises an antibody-derived binding site, such as a scFv. Alternatively the binding site may be based on a ligand for the target antigen.

The CAR may specifically bind a tumour-associated cell-surface antigen.

Various tumour associated antigens (TAA) are known, some of which are shown in Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Spacer

The chimeric antigen receptor may comprise a spacer to connect the antigen-binding domain with the transmembrane domain and spatially separate the antigen-binding domain from the endodomain. A flexible spacer allows to the antigen-binding domain to orient in different directions to enable antigen binding.

The spacer sequence may, for example, comprise an IgG1 Fc region, an IgG1 hinge or a CD8 stalk. The linker may alternatively comprise an alternative linker sequence which has similar length and/or domain spacing properties as an IgG1 Fc region, an IgG1 hinge or a CD8 stalk.

Transmembrane Domain

The transmembrane domain is the sequence of a CAR that spans the membrane. It may comprise a hydrophobic alpha helix. The transmembrane domain may be derived from CD19 or CD28 (which gives good receptor stability).

Car Signal Peptide

The CAR described herein may comprise a signal peptide so that when it is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

Car Endodomain

The endodomain is the portion of a CAR which is located on the intracellular side of the membrane.

The endodomain is the signal-transmission portion of a CAR. After antigen recognition by the antigen binding domain, individual CAR molecules cluster, native CD45 and CD148 are excluded from the synapse and a signal is transmitted to the cell.

The CAR endodomain may be or comprise an intracellular signalling domain. In an alternative embodiment, the endodomain of the present CAR may be capable of interacting with an intracellular signalling molecule which is present in the cytoplasm, leading to signalling.

The most commonly used signalling domain component is that of CD3-zeta endodomain, which contains three ITAMs. This transmits an activation signal to the T cell after antigen is bound. CD3-zeta may not provide a fully competent activation signal and additional co-stimulatory signalling may be needed. For example, the CAR may also comprise an endodomain from OX40 or 41 BB. The CAR may alternatively or additional comprise an endodomain from CD28.

The CAR endodomain may alternatively or additionally comprise one or more of the following: an ICOS endodomain, a CD27 endodomain, a BTLA endodomain, a CD30 endodomain, a GITR endodomain and an HVEM endodomain.

Nucleic Acid

The present invention provides a nucleotide sequence encoding a constitutively active STAT or an inducible STAT molecule of the invention.

Nucleic Acid Construct

The present invention further provides a nucleotide construct comprising a first nucleotide sequence encoding a constitutively active STAT or inducible STAT molecule, along with a second nucleotide sequence encoding a CAR.

The nucleic acid construct may comprise a cleavage site, such that the STAT molecule and CAR are expressed as separate polypeptides As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

Vector

The present invention also provides a vector, which comprises a nucleic acid sequence(s) or nucleic acid construct of the invention. The vector may be used to introduce the nucleic acid sequence(s) into a host cell so that it expresses a CAR and a STAT molecule according to the first aspect of the invention.

The vector may, for example, be a plasmid or a viral vector, such as a retroviral vector or a lentiviral vector, or a transposon based vector or synthetic mRNA. The vector may be capable of transfecting or transducing a T cell or a NK cell.

Cell

The present invention provides a cell which comprises a CAR and a constitutively active or inducible STAT molecule.

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR-expressing cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR and STAT molecule-expressing cells are generated by introducing DNA or RNA coding for the CAR and STAT molecule by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR and constitutively active STAT molecule according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a CAR.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The present invention provides a CAR and constitutively active or inducible STAT molecule-expressing cell of the present invention for use in treating and/or preventing a disease.

The invention also relates to the use of a CAR and the constitutively active or inducible STAT molecule expressing cell of the present invention in the manufacture of a medicament for the treatment and/or prevention of a disease.

The disease to be treated and/or prevented by the methods of the present invention may be a cancerous disease, such as Acute lymphoblastic leukemia (ALL), chronic lymphoblastic leukemia (CLL), bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

The cells and pharmaceutical compositions of present invention may be for use in any of the methods described above.

Cell Comprising a Car and a Constitutively Active or Inducible Janus Kinase (Jak) Molecule The present invention also provides a cell comprising a chimeric antigen receptor (CAR) and a constitutively active or inducible JAK molecule.

The sections above relating to nucleotide sequences and constructs, vectors, pharmaceutical compositions and uses thereof, and methods also apply to the cell of the present invention which comprises a CAR and a constitutively active or inducible JAK molecule.

The invention will now be further described by way of Examples, which are meant to serve to assist one of ordinary skill in the art in carrying out the invention and are not intended in any way to limit the scope of the invention.

EXAMPLES

T-cell persistence, engraftment and exhaustion are tested in standard in vitro and in vivo assays.

Example 1: In Vitro Testing

In vitro assays comprise of a series of repetitive stimulation assays. T cells are transduced with target cells (e.g., anti-CD19 CAR) expressing the cognate ligand for 84 hours at a 1:1 target to effector ratio.

During this period of time, the rate of target cell cytolysis is assessed using automated real-time florescence measurements of the target cells. After co-incubation, the supernatant is used to measure IFN-γ release. In addition, the CAR T-cells are collected, counted and assessed for differentiation markers (e.g., CD45RA, CCR7) and exhaustion markers (e.g., PD1, Tim3 or LAGS) and then re-challenged with new target cells for a further 84 hours.

The process is repeated with several rounds of stimulation and assessed until there are not enough CAR T-cells to proceed due to a lack of proliferation or T-cell death. Proliferation of T cells and T-cell death is determined using automated real-time fluorescence measurements of the target cells.

Example 2: In Vivo Testing

In vivo assays comprise of standard immune competent mouse models where tumour is subcutaneously injected and the ability for T-cells to eliminate the tumour is assess over a period of two to ten weeks. By way of example, the assays comprise of orthotropic glioma mouse model expressing the cognate ligand EGFRVIII.

Mice are used in re-inoculation studies and surviving CAR T cells are used in adoptive cell transfer experiments where CAR T-cells from a cured mouse are transferred into a newly inoculated mouse to assess CAR T cell exhaustion. Further, engraftment/expansion of T-cells at the tumour bed or within lymphoid tissues such as lymph nodes, spleen and bone-marrow measured by flow cytometry and bioluminescence imaging of said tissues.

Example 3: Testing the Inducible and Constitutively Active STAT Constructs

A panel of constructs comprising the inducible or constitutively active STAT are placed in conjunction with a CAR directed against CD19 and subjected to an in vitro assay described in Example 1, comprising of a series of repetitive stimulations. The constitutively active STAT constructs depicted in FIGS. 5(a) and (b) comprise regions encoding an anti-CD19 CAR (aCD19) and are subjected to the same in vitro assay. The transduced T cells are challenged with target cells expressing CD19 for 84 hours at a 1:1 target to effector ratio, as described above.

SEQ ID NO: 7 is used to test the construct depicted in FIG. 3(c).

SEQ ID NO: 8 is used to test the construct depicted in FIG. 4.

SEQ ID NOs: 9 and 10 are used to test the constructs depicted in FIGS. 5(a) and (b).

SEQ ID Nos: 11 and 12 are used to test the constructs depicted in FIGS. 6(a) and (b).

The constitutively active STAT constructs tested in Example 3 comprise the following amino acid sequences:

```
(STAT3-Linker-STAT5)
                                                          SEQ ID NO: 7
AQWNQLQQLDTRYLEQLHQLYSDSFPMELRQFLAPWIESQDWAYAASKESHATLV

FHNLLGEIDQQYSRFLQESNVLYQHNLRRIKQFLQSRYLEKPMEIARIVARCLWEES

RLLQTAATAAQQGGQANHPTAAVVTEKQQMLEQHLQDVRKRVQDLEQKMKVVENL

QDDFDFNYKTLKSQGDMQDLNGNNQSVTRQKMQQLEQMLTALDQMRRSIVSELA

GLLSAMEYVQKTLTDEELADWKRRQQIACIGGPPNICLDRLENWITSLAESQLQTRQ

QIKKLEELQQKVSYKGDPIVQHRPMLEERIVELFRNLMKSAFVVERQPCMPMHPDR

PLVIKTGVQFTTKVRLLVKFPELNYQLKIKVCIDKDSGDVAALRGSRKFNILGTNTKVM

NMEESNNGSLSAEFKHLTLREQRCGNGGRANCDASLIVTEELHLITFETEVYHQGLK

IDLETHSLPVVVISNICQMPNAWASILWYNMLTNNPKNVNFFTKPPIGTWDQVAEVLS

WQFSSTTKRGLSIEQLTTLAEKLLGPGVNYSGCQITWAKFCKENMAGKGFSFWVWL

DNIIDLVKKYILALWNEGYIMGFISKERERAILSTKPPGTFLLRFSESSKEGGVTFTWV

EKDISGKTQIQSVEPYTKQQLNNMSFAEIIMGYKIMDATNILVSPLVYLYPDIPKEEAF

GKYCRPESQEHPEADPGSAAPYLKTKFICVTPTTCSNTIDLPMSPRTLDSLMQFGNN

GEGAEPSAGGQFESLTFDMELTSECATSPMSGGGGSGGGGSGGGGSGGGGSGG

GGSMAGWIQAQQLQGDALRQMQVLYGQHFPIEVRHYLAQWIESQPWDAIDLDNPQ

DRAQATQLLEGLVQELQKKAEHQVGEDGFLLKIKLGHYATQLQKTYDRCPLELVRCI

RHILYNEQRLVREANNCSSPAGILVDAMSQKHLQINQTFEELRLVTQDTENELKKLQ

QTQEYFIIQYQESLRIQAQFAQLAQLSPQERLSRETALQQKQVSLEAWLQREAQTLQ

QYRVELAEKHQKTLQLLRKQQTIILDDELIQWKRRQQLAGNGGPPEGSLDVLQSWC

EKLAEIIWQNRQQIRRAEHLCQQLPIPGPVEEMLAEVNATITDIISALVTSTFIIEKQPP

QVLKTQTKFAATVRLLVGGKLNVHMNPPQVKATIISEQQAKSLLKNENTRNECSGEIL

NNCCVMEYHQATGTLSAHFRNMSLKRIKRADRRGAESVTEEKFTVLFESQFSVGSN

ELVFQVKTLSLPVVVIVHGSQDHNATATVLWDNAFAEPGRVPFAVPDKVLWPQLCE

ALNMKFKAEVQSNRGLTKENLVFLAQKLFNNSSSHLEDYSGLSVSWSQFNRENLPG

WNYTFWQWFDGVMEVLKKHHKPHWNDGAILGFVNKQQAHDLLINKPDGTFLLRFS

DSEIGGITIAWKFDSPERNLWNLKPFTTRDFSIRSLADRLGDLSYLIYVFPDRPKDEVF

SKYYTPVLAKAVDGYVKPQIKQVVPEFVNASADAGGSSATYMDQAPSPAVCPQAPY

NMYPQNPDHVLDQDGEFDLDETMDVARHVEELLRRPMDSLDSRLSPPAGLFTSAR

GSLS
```

-continued (TIP-STAT3-Linker-STAT5-2a-Myristoylation and palmitoylation sequence-Ridge Linker-TetRB)
SEQ ID NO: 8

MWTWNAYAFAAPSGGGSAQWNQLQQLDTRYLEQLHQLYSDSFPMELRQFLAPWI

ESQDWAYAASKESHATLVFHNLLGEIDQQYSRFLQESNVLYQHNLRRIKQFLQSRYL

EKPMEIARIVARCLWEESRLLQTAATAAQQGGQANHPTAAVVTEKQQMLEQHLQDV

RKRVQDLEQKMKVVENLQDDFDFNYKTLKSQGDMQDLNGNNQSVTRQKMQQLEQ

MLTALDQMRRSIVSELAGLLSAMEYVQKTLTDEELADWKRRQQIACIGGPPNICLDR

LENWITSLAESQLQTRQQIKKLEELQQKVSYKGDPIVQHRPMLEERIVELFRNLMKS

AFVVERQPCMPMHPDRPLVIKTGVQFTTKVRLLVKFPELNYQLKIKVCIDKDSGDVA

ALRGSRKFNILGTNTKVMNMEESNNGSLSAEFKHLTLREQRCGNGGRANCDASLIV

TEELHLITFETEVYHQGLKIDLETHSLPVVVISNICQMPNAWASILWYNMLTNNPKNV

NFFTKPPIGTWDQVAEVLSWQFSSTTKRGLSIEQLTTLAEKLLGPGVNYSGCQITWA

KFCKENMAGKGFSFWVWLDNIIDLVKKYILALWNEGYIMGFISKERERAILSTKPPGT

FLLRFSESSKEGGVTFTWVEKDISGKTQIQSVEPYTKQQLNNMSFAEIIMGYKIMDAT

NILVSPLVYLYPDIPKEEAFGKYCRPESQEHPEADPGSAAPYLKTKFICVTPTTCSNTI

DLPMSPRTLDSLMQFGNNGEGAEPSAGGQFESLTFDMELTSECATSPMSGGGGS

GGGGGGGSGGGGSGGGGSMAGWIQAQQLQGDALRQMVLYGQHFPIEVRHY

LAQWIESQPWDAIDLDNPQDRAQATQLLEGLVQELQKKAEHQVGEDGFLLKIKLGH

YATQLQKTYDRCPLELVRCIRHILYNEQRLVREANNCSSPAGILVDAMSQKHLQINQ

TFEELRLVTQDTENELKKLQQTQEYFIIQYQESLRIQAQFAQLAQLSPQERLSRETAL

QQKQVSLEAWLQREAQTLQQYRVELAEKHQKTLQLLRKQQTIILDDELIQWKRRQQ

LAGNGGPPEGSLDVLQSWCEKLAEIIWQNRQQIRRAEHLCQQLPIPGPVEEMLAEV

NATITDIISALVTSTFIIEKQPPQVLKTQTKFAATVRLLVGGKLNVHMNPPQVKATIISE

QQAKSLLKNENTRNECSGEILNNCCVMEYHQATGTLSAHFRNMSLKRIKRADRRGA

ESVTEEKFTVLFESQFSVGSNELVFQVKTLSLPVVVIVHGSQDHNATATVLWDNAFA

EPGRVPFAVPDKVLWPQLCEALNMKFKAEVQSNRGLTKENLVFLAQKLFNNSSSHL

EDYSGLSVSWSQFNRENLPGWNYTFWQWFDGVMEVLKKHHKPHWNDGAILGFVN

KQQAHDLLINKPDGTFLLRFSDSEIGGITIAWKFDSPERNLWNLKPFTTRDFSIRSLA

DRLGDLSYLIYVFPDRPKDEVFSKYYTPVLAKAVDGYVKPQIKQVVPEFVNASADAG

GSSATYMDQAPSPAVCPQAPYNMYPQNPDHVLDQDGEFDLDETMDVARHVEELL

RRPMDSLDSRLSPPAGLFTSARGSLSEGRGSLLTCGDVEENPGPMGCGCSSHPEL

EAEAAAKEAAAKEAAAKEAAAKALEAEAAAKEAAAKEAAAKEAAAKALESGGGSMS

RLDKSKVINSALELLNEVGIEGLTTRKLAQKLGVEQPTLYWHVKNKRALLDALAIEML

DRHHTHFCPLEGESWQDFLRNNAKSFRCALLSHRDGAKVHLGTRPTEKQYETLEN

QLAFLCQQGFSLENALYALSAVGHFTLGCVLEDQEHQVAKEERETPTTDSMPPLLR

QAIELFDHQGAEPAFLFGLELIICGLEKQLKCESGS (SH2 ZAP70-Linker-TEV-2a-myristoylation and palmitoylation sequence-linker-TEV cleavage site x3-STAT3-Linker-STAT5-2a-aCD19)
SEQ ID NO: 9

MPDPAAHLPFFYGSISRAEAEEHLKLAGMADGLFLLRQCLRSLGGYVLSLVHDVRFH

HFPIERQLNGTYAIAGGKAHCGPAELCEFYSRDPDGLPCNLRKPCNRPSGLEPQPG

VFDCLRDAMVRDYVRQTWKLEGEALEQAIISQAPQVEKLIATTAHERMPWYHSSLT

REEAERKLYSGAQTDGKFLLRPRKEQGTYALSLIYGKTVYHYLISQDKAGKYCIPEG

-continued

```
TKFDTLWQLVEYLKLKADGLIYCLKEACPNSSASNASGAAAPTLPAHPSTLTHPSGG
GGSSLFKGPRDYNPISSTICHLTNESDGHTTSLYGIGFGPFIITNKHLFRRNNGTLLVQ
SLHGVFKVKNTTTLQQHLIDGRDMIIRMPKDFPPFPQKLKFREPQREERICLVTTNF
QTKSMSSMVSDTSCTFPSSDGIFWKHWIQTKDGQCGSPLVSTRDGFIVGIHSASNF
TNTNNYFTSVPKNFMELLTNQEAQQWVSGWRLNADSVLWGGHKVFMSKPEEPFQ
PVKEATQLMNELVYSQEGRGSLLTCGDVEENPGPMGCGCSSHPESGGGGSGGG
GSENLYFQGENLYFQGENLYFQGENLYFQGENLYFQGENLYFQGENLYFQGENLY
FQGENLYFQGAQWNQLQQLDTRYLEQLHQLYSDSFPMELRQFLAPWIESQDWAYA
ASKESHATLVFHNLLGEIDQQYSRFLQESNVLYQHNLRRIKQFLQSRYLEKPMEIARI
VARCLWEESRLLQTAATAAQQGGQANHPTAAVVTEKQQMLEQHLQDVRKRVQDL
EQKMKVVENLQDDFDFNYKTLKSQGDMQDLNGNNQSVTRQKMQQLEQMLTALDQ
MRRSIVSELAGLLSAMEYVQKTLTDEELADWKRRQQIACIGGPPNICLDRLENWITSL
AESQLQTRQQIKKLEELQQKVSYKGDPIVQHRPMLEERIVELFRNLMKSAFVVERQP
CMPMHPDRPLVIKTGVQFTTKVRLLVKFPELNYQLKIKVCIDKDSGDVAALRGSRKF
NILGTNTKVMNMEESNNGSLSAEFKHLTLREQRCGNGGRANCDASLIVTEELHLITF
ETEVYHQGLKIDLETHSLPVVVISNICQMPNAWASILWYNMLTNNPKNVNFFTKPPIG
TWDQVAEVLSWQFSSTTKRGLSIEQLTTLAEKLLGPGVNYSGCQITWAKFCKENMA
GKGFSFWVWLDNIIDLVKKYIALWNEGYIMGFISKERERAILSTKPPGTFLLRFSESS
KEGGVTFTWVEKDISGKTQIQSVEPYTKQQLNNMSFAEIIMGYKIMDATNILVSPLVY
LYPDIPKEEAFGKYCRPESQEHPEADPGSAAPYLKTKFICVTPTTCSNTIDLPMSPRT
LDSLMQFGNNGEGAEPSAGGQFESLTFDMELTSECATSPMSGGGGSGGGGSGG
GGSGGGGSGGGGSMAGWIQAQQLQGDALRQMQVLYGQHFPIEVRHYLAQWIESQ
PWDAIDLDNPQDRAQATQLLEGLVQELQKKAEHQVGEDGFLLKIKLGHYATQLQKT
YDRCPLELVRCIRHILYNEQRLVREANNCSSPAGILVDAMSQKHLQINQTFEELRLVT
QDTENELKKLQQTQEYFIIQYQESLRIQAQFAQLAQLSPQERLSRETALQQKQVSLE
AWLQREAQTLQQYRVELAEKHQKTLQLLRKQQTIILDDELIQWKRRQQLAGNGGPP
EGSLDVLQSWCEKLAEIIWQNRQQIRRAEHLCQQLPIPGPVEEMLAEVNATITDIISAL
VTSTFIIEKQPPQVLKTQTKFAATVRLLVGGKLNVHMNPPQVKATIISEQQAKSLLKN
ENTRNECSGEILNNCCVMEYHQATGTLSAHFRNMSLKRIKRADRRGAESVTEEKFT
VLFESQFSVGSNELVFQVKTLSLPVVVIVHGSQDHNATATVLWDNAFAEPGRVPFA
VPDKVLWPQLCEALNMKFKAEVQSNRGLTKENLVFLAQKLFNNSSSHLEDYSGLSV
SWSQFNRENLPGWNYTFWQWFDGVMEVLKKHHKPHWNDGAILGFVNKQQAHDLL
INKPDGTFLLRFSDSEIGGITIAWKFDSPERNLWNLKPFTTRDFSIRSLADRLGDLSYL
IYVFPDRPKDEVFSKYYTPVLAKAVDGYVKPQIKQVVPEFVNASADAGGSSATYMD
QAPSPAVCPQAPYNMYPQNPDHVLDQDGEFDLDETMDVARHVEELLRRPMDSLDS
RLSPPAGLFTSARGSLSEGRGSLLTCGDVEENPGPMETDTLLLWVLLLWVPGSTGD
IQMTQTTSSLSASLGDRVTISCRASQDISKYLNWYQQKPDGTVKLLIYHTSRLHSGV
PSRFSGSGSGTDYSLTISNLEQEDIATYFCQQGNTLPYTFGGGTKLEITKAGGGGSG
GGGSGGGGSGGGGSEVKLQESGPGLVAPSQSLSVTCTVSGVSLPDYGVSWIRQP
PRKGLEWLGVIWGSETTYYNSALKSRLTIIKDNSKSQVFLKMNSLQTDDTAIYYCAKH
```

-continued

YYYGGSYAMDYWGQGTSVTVSSDPTTTPAPRPPTPAPTIASQPLSLRPEACRPAAG

GAVHTRGLDFACDIYIWAPLAGTCGVLLLSLVITLYCKRGRKKLLYIFKQPFMRPVQT

TQEEDGCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGKGHDG

LYQGLSTATKDTYDALHMQALPPR (TIP-Linker-dZap70SH2-linker-TEV-2a-Truncated CD22-CD19TM-Tyro-1
endodomain-Linker-TetRB-2A-aCD19-linker-TEV cleavage site x 3-
GOFSTAT5(S710F)

SEQ ID NO: 10

MWTWNAYAFAAPSGGGSMPDPAAHLPFFYGSISRAEAEEHLKLAGMADGLFLLRQ

CLRSLGGYVLSLVHDVRFHHFPIERQLNGTYAIAGGKAHCGPAELCEFYSRDPDGLP

CNLRKPCNRPSGLEPQPGVFDCLRDAMVRDYVRQTWKLEGEALEQAIISQAPQVEK

LIATTAHERMPWYHSSLTREEAERKLYSGAQTDGKFLLRPRKEQGTYALSLIYGKTV

YHYLISQDKAGKYCIPEGTKFDTLWQLVEYLKLKADGLIYCLKEACPNSSASNASGA

AAPTLPAHPSTLTHPSGGGGSSLFKGPRDYNPISSTICHLTNESDGHTTSLYGIGFG

PFIITNKHLFRRNNGTLLVQSLHGVFKVKNTTTLQQHLIDGRDMIIRMPKDFPPFPQK

LKFREPQREERICLVTTNFQTKSMSSMVSDTSCTFPSSDGIFWKHWIQTKDGQCGS

PLVSTRDGFIVGIHSASNFTNTNNYFTSVPKNFMELLTNQEAQQWVSGWRLNADSV

LWGGHKVFMSKPEEPFQPVKEATQLMNELVYSQEGRGSLLTCGDVEENPGPMET

DTLLLWVLLLWVPGSTGDSSGKPIPNPLLGLDSSGGGSAPRDVRVRKIKPLSEIHSG

NSVSLQCDFSSSHPKEVQFFWEKNGRLLGKESQLNFDSISPEDAGSYSCWVNNSIG

QTASKAWTLEVLYAPRRLRVSMSPGDQVMEGKSATLTCESDANPPVSHYTWFDW

NNQSLPYHSQKLRLEPVKVQHSGAYWCQGTNSVGKGRSPLSTLTVYYSPETIGRR

AVTLAYLIFCLCSLVGILHLRARRSMDEANQPLLTDQYQCYAEEYEKLQNPNQSVV

GGSGGSMSRLDKSKVINSALELLNEVGIEGLTTRKLAQKLGVEQPTLYWHVKNKRAL

LDALAIEMLDRHHTHFCPLEGESWQDFLRNNAKSFRCALLSHRDGAKVHLGTRPTE

KQYETLENQLAFLCQQGFSLENALYALSAVGHFTLGCVLEDQEHQVAKEERETPTT

DSMPPLLRQAIELFDHQGAEPAFLFGLELIICGLEKQLKCESGSEGRGSLLTCGDVEE

NPGPMETDTLLLWVLLLWVPGSTGDIQMTQTTSSLSASLGDRVTISCRASQDISKYL

NWYQQKPDGTVKLLIYHTSRLHSGVPSRFSGSGSGTDYSLTISNLEQEDIATYFCQQ

GNTLPYTFGGGTKLEITKAGGGGSGGGGSGGGGSGGGGSEVKLQESGPGLVAPS

QSLSVTCTVSGVSLPDYGVSWIRQPPRKGLEWLGVIWGSETTYYNSALKSRLTIIKD

NSKSQVFLKMNSLQTDDTAIYYCAKHYYYGGSYAMDYWGQGTSVTVSSDPTTTPA

PRPPTPAPTIASQPLSLRPEACRPAAGGAVHTRGLDFACDIYIWAPLAGTCGVLLLSL

VITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPRGGSG

GSENLYFQGENLYFQGENLYFQGENLYFQGENLYFQGENLYFQGENLYFQGENLY

FQGENLYFQGMAGWIQAQQLQGDALRQMVLYGQHFPIEVRHYLAQWIESQPWD

AIDLDNPQDRAQATQLLEGLVQELQKKAEHQVGEDGFLLKIKLGHYATQLQKTYDRC

PLELVRCIRHILYNEQRLVREANNCSSPAGILVDAMSQKHLQINQTFEELRLVTQDTE

NELKKLQQTQEYFIIQYQESLRIQAFAQLAQLSPQERLSRETALQQKQVSLEAWLQ

REAQTLQQYRVELAEKHQKTLQLLRKQQTIILDDELIQWKRRQQLAGNGGPPEGSL

-continued

```
DVLQSWCEKLAEIIWQNRQQIRRAEHLCQQLPIPGPVEEMLAEVNATITDIISALVTST

FIIEKQPPQVLKTQTKFAATVRLLVGGKLNVHMNPPQVKATIISEQQAKSLLKNENTR

NECSGEILNNCCVMEYHQATGTLSAHFRNMSLKRIKRADRRGAESVTEEKFTVLFE

SQFSVGSNELVFQVKTLSLPVVVIVHGSQDHNATATVLWDNAFAEPGRVPFAVPDK

VLWPQLCEALNMKFKAEVQSNRGLTKENLVFLAQKLFNNSSSHLEDYSGLSVSWS

QFNRENLPGWNYTFWQWFDGVMEVLKKHHKPHWNDGAILGFVNKQQAHDLLINK

PDGTFLLRFSDSEIGGITIAWKFDSPERNLWNLKPFTTRDFSIRSLADRLGDLSYLIYV

FPDRPKDEVFSKYYTPVLAKAVDGYVKPQIKQVVPEFVNAFADAGGSSATYMDQAP

SPAVCPQAPYNMYPQNPDHVLDQDGEFDLDETMDVARHVEELLRRPMDSLDSRLS

PPAGLFTSARGSLS
```

The inducible STAT constructs tested comprise the following amino acid sequence:

```
(FRB-linker-STAT5-2a-FKBP12-linker-STAT3)
                                           SEQ ID NO: 11
ILWHEMWHEGLEEASRLYFGERNVKGMFEVLEPLHAMMERGPQTLKETSFNQAYG

RDLMEAQEWCRKYMKSGNVKDLLQAWDLYYHVFRRISKSGGGGSGGGGSGGGG

SMAGWIQAQQLQGDALRQMQVLYGQHFPIEVRHYLAQWIESQPWDAIDLDNPQDR

AQATQLLEGLVQELQKKAEHQVGEDGFLLKIKLGHYATQLQKTYDRCPLELVRCIRHI

LYNEQRLVREANNCSSPAGILVDAMSQKHLQINQTFEELRLVTQDTENELKKLQQTQ

EYFIIQYQESLRIQAQFAQLAQLSPQERLSRETALQQKQVSLEAWLQREAQTLQQYR

VELAEKHQKTLQLLRKQQTIILDDELIQWKRRQQLAGNGGPPEGSLDVLQSWCEKL

AEIIWQNRQQIRRAEHLCQQLPIPGPVEEMLAEVNATITDIISALVTSTFIIEKQPPQVL

KTQTKFAATVRLLVGGKLNVHMNPPQVKATIISEQQAKSLLKNENTRNECSGEILNN

CCVMEYHQATGTLSAHFRNMSLKRIKRADRRGAESVTEEKFTVLFESQFSVGSNEL

VFQVKTLSLPVVVIVHGSQDHNATATVLWDNAFAEPGRVPFAVPDKVLWPQLCEAL

NMKFKAEVQSNRGLTKENLVFLAQKLFNNSSSHLEDYSGLSVSWSQFNRENLPGW

NYTFWQWFDGVMEVLKKHHKPHWNDGAILGFVNKQQAHDLLINKPDGTFLLRFSD

SEIGGITIAWKFDSPERNLWNLKPFTTRDFSIRSLADRLGDLSYLIYVFPDRPKDEVFS

KYYTPVLAKAVDGYVKPQIKQVVPEFVNASADAGGSSATYMDQAPSPAVCPQAPYN

MYPQNPDHVLDQDGEFDLDETMDVARHVEELLRRPMDSLDSRLSPPAGLFTSARG

SLSEGRGSLLTCGDVEENPGPGVQVETISPGDGRTFPKRGQTCVVHYTGMLEDGK

KVDSSRDRNKPFKFMLGKQEVIRGWEEGVAQMSVGQRAKLTISPDYAYGATGHPGI

IPPHATLVFDVELLKLESGGGGSGGGGSGGGGSAQWNQLQQLDTRYLEQLHQLYS

DSFPMELRQFLAPWIESQDWAYAASKESHATLVFHNLLGEIDQQYSRFLQESNVLY

QHNLRRIKQFLQSRYLEKPMEIARIVARCLWEESRLLQTAATAAQQGGQANHPTAA

VVTEKQQMLEQHLQDVRKRVQDLEQKMKVVENLQDDFDFNYKTLKSQGDMQDLN

GNNQSVTRQKMQQLEQMLTALDQMRRSIVSELAGLLSAMEYVQKTLTDEELADWK

RRQQIACIGGPPNICLDRLENWITSLAESQLQTRQQIKKLEELQQKVSYKGDPIVQHR

PMLEERIVELFRNLMKSAFVVERQPCMPMHPDRPLVIKTGVQFTTKVRLLVKFPELN

YQLKIKVCIDKDSGDVAALRGSRKFNILGTNTKVMNMEESNNGSLSAEFKHLTLREQ
```

```
RCGNGGRANCDASLIVTEELHLITFETEVYHQGLKIDLETHSLPVVVISNICQMPNAW

ASILWYNMLTNNPKNVNFFTKPPIGTWDQVAEVLSWQFSSTTKRGLSIEQLTTLAEK

LLGPGVNYSGCQITWAKFCKENMAGKGFSFWVWLDNIIDLVKKYILALWNEGYIMGF

ISKERERAILSTKPPGTFLLRFSESSKEGGVTFTWVEKDISGKTQIQSVEPYTKQQLN

NMSFAEIIMGYKIMDATNILVSPLVYLYPDIPKEEAFGKYCRPESQEHPEADPGSAAP

YLKTKFICVTPTTCSNTIDLPMSPRTLDSLMQFGNNGEGAEPSAGGQFESLTFDMEL

TSECATSPM (TIP-linker-STAT5-2a-TetRB-linker-STAT3)
                                                    SEQ ID NO: 12
MWTWNAYAFAAPSGGGGSGGGGSGGGGSMAGWIQAQQLQGDALRQMQVLYGQ

HFPIEVRHYLAQWIESQPWDAIDLDNPQDRAQATQLLEGLVQELQKKAEHQVGEDG

FLLKIKLGHYATQLQKTYDRCPLELVRCIRHILYNEQRLVREANNCSSPAGILVDAMS

QKHLQINQTFEELRLVTQDTENELKKLQQTQEYFIIQYQESLRIQAQFAQLAQLSPQE

RLSRETALQQKQVSLEAWLQREAQTLQQYRVELAEKHQKTLQLLRKQQTIILDDELI

QWKRRQQLAGNGGPPEGSLDVLQSWCEKLAEIIWQNRQQIRRAEHLCQQLPIPGP

VEEMLAEVNATITDIISALVTSTFIIEKQPPQVLKTQTKFAATVRLLVGGKLNVHMNPP

QVKATIISEQQAKSLLKNENTRNECSGEILNNCCVMEYHQATGTLSAHFRNMSLKRI

KRADRRGAESVTEEKFTVLFESQFSVGSNELVFQVKTLSLPVVVIVHGSQDHNATAT

VLWDNAFAEPGRVPFAVPDKVLWPQLCEALNMKFKAEVQSNRGLTKENLVFLAQKL

FNNSSSHLEDYSGLSVSWSQFNRENLPGWNYTFWQWFDGVMEVLKKHHKPHWN

DGAILGFVNKQQAHDLLINKPDGTFLLRFSDSEIGGITIAWKFDSPERNLWNLKPFTT

RDFSIRSLADRLGDLSYLIYVFPDRPKDEVFSKYYTPVLAKAVDGYVKPQIKQVVPEF

VNASADAGGSSATYMDQAPSPAVCPQAPYNMYPQNPDHVLDQDGEFDLDETMDV

ARHVEELLRRPMDSLDSRLSPPAGLFTSARGSLSEGRGSLLTCGDVEENPGPMSRL

DKSKVINSALELLNEVGIEGLTTRKLAQKLGVEQPTLYWHVKNKRALLDALAIEMLDR

HHTHFCPLEGESWQDFLRNNAKSFRCALLSHRDGAKVHLGTRPTEKQYETLENQL

AFLCQQGFSLENALYALSAVGHFTLGCVLEDQEHQVAKEERETPTTDSMPPLLRQAI

ELFDHQGAEPAFLFGLELIICGLEKQLKCESGSSGGGGSGGGGSGGGGSAQWNQL

QQLDTRYLEQLHQLYSDSFPMELRQFLAPWIESQDWAYAASKESHATLVFHNLLGEI

DQQYSRFLQESNVLYQHNLRRIKQFLQSRYLEKPMEIARIVARCLWEESRLLQTAAT

AAQQGGQANHPTAAVVTEKQQMLEQHLQDVRKRVQDLEQKMKVVENLQDDFDFN

YKTLKSQGDMQDLNGNNQSVTRQKMQQLEQMLTALDQMRRSIVSELAGLLSAMEY

VQKTLTDEELADWKRRQQIACIGGPPNICLDRLENWITSLAESQLQTRQQIKKLEELQ

QKVSYKGDPIVQHRPMLEERIVELFRNLMKSAFVVERQPCMPMHPDRPLVIKTGVQ

FTTKVRLLVKFPELNYQLKIKVCIDKDSGDVAALRGSRKFNILGTNTKVMNMEESNN

GSLSAEFKHLTLREQRCGNGGRANCDASLIVTEELHLITFETEVYHQGLKIDLETHSL

PVVVISNICQMPNAWASILWYNMLTNNPKNVNFFTKPPIGTWDQVAEVLSWQFSST

TKRGLSIEQLTTLAEKLLGPGVNYSGCQITWAKFCKENMAGKGFSFWVWLDNIIDLV

KKYILALWNEGYIMGFISKERERAILSTKPPGTFLLRFSESSKEGGVTFTWVEKDISG

KTQIQSVEPYTKQQLNNMSFAEIIMGYKIMDATNILVSPLVYLYPDIPKEEAFGKYCRP

ESQEHPEADPGSAAPYLKTKFICVTPTTCSNTIDLPMSPRTLDSLMQFGNNGEGAEP

SAGGQFESLTFDMELTSECATSPM
```

The process is repeated with several rounds of stimulation and assessed until there are not enough CAR T-cells to proceed due to a lack of proliferation or T-cell death. Proliferation of T cells and T-cell death is determined using T-cell counts and stains for apoptosis and necrosis (e.g. Annexin IV and 7AAD).

The same constructs used in in vitro testing are used to test function in vivo with an additional construct transduced into the CAR T cells encoding for firefly luciferase to visualise the CAR T cell population in situ.

In vivo assays comprise of standard immune competent mouse models where tumour is orthotopically or subcutaneously injected and the ability for T-cells to eliminate the tumour is assessed over a period of two to ten weeks. GL261 cell lines are transduced to express the cognate ligand human CD19 and then intracranially injected into C57131/6 mice. On day 11 post tumour implantation, mice received 5Gy total body irradiation followed by an intravenous injection of CAR T cells.

FIGS. 7, 8, 9, 10, 11 and 12 provide annotated sequences of SEQ ID Nos 7, 8, 9, 10, 11 and 12, respectively.

Example 4: Assessment of the Propensity to Proliferate of Cells Expressing a Constitutively Active STAT Molecule in the Absence of Stimulation Measured by CTV Dilution A 96-hour starvation assay was set up comprising of peripheral blood mononuclear cells (PBMCs) labelled with cell trace violet (CTV). Cells were cultured in complete media in the absence of stimulation and exogenous cytokines (IL2). The cells were then analysed by flow cytometry on day 4, and the CTV mean fluorescence intensity (MFI) value calculated (gated on singlet, CD3+, live cells). When cells were transduced with a STAT encoding construct, the value of the MFI was gated on the transduced population. The CTV MFI is inversely proportional to the number of cellular divisions. The control (mock) refers to the total CD3 population from non-transduced PBMCs.

The constitutively active STAT molecule tested (STAT5beta R659C gain of function mutation) demonstrated decreased CTV dilution values compared to the wild type constructs (STAT5beta_WT) which demonstrates that this mutant has increased propensity to proliferate compared to the wild type constructs (FIG. 13).

Example 5: Assessment of Intracellular Phosphorylated STAT5beta of Cells Expressing Constitutively Active STAT Mutants Constructs Compared to Wild Type A 72-hour starvation assay was set up to analyse intracellular staining for phosphorylated STAT5 (pSTAT5_Y694). Cells were cultured in complete media in the absence of stimulation and exogenous cytokines for 3 days. Afterwards, the cells were fixed and permeabilized and stained with the pSTAT5_Y694 antibody in accordance to BD Pharmingen phospho-FLOW protocol.

The cells were then analysed by flow cytometry and the pSTAT5 value was calculated (gated on singlet, CD3+, live cells).

Both the STAT5beta T628S and the STAT5beta1704F gain of function (GOF) mutations showed a greater area under the curve in the histograms of FIGS. 14 (*a*) and (*b*), respectively, compared to the wild type STAT5beta constructs or controls.

Example 6: Assessment of the Capacity of Cells Expressing Constitutively Active STAT5 Mutants to Induce STAT5 Dependent Gene Expression A STAT5 responsive GFP reporter cell line was generated by transducing 293T cells with a self-inactivating vector construct. The vector comprised of three STAT5 DNA responsive elements controlling the expression of GFP followed by a constitutively active PGK promoter and a marker of transduction Q8 (doi.org/10.1182). The reporter cell line was transfected with the constructs encoding STAT and JAK mutants and GFP expression assessed 3 days later via flow cytometry.

FIGS. 15(*a*) and (*b*) both show an increase in GFP expression for the constitutively activate JAK2 and STAT5beta constructs (GOF mutants), respectively, compared to the corresponding wild type constructs.

The dotted horizontal lines on each on the bar graphs of FIGS. 15(*a*) and 15(*b*) represent background expression.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING

```
Sequence total quantity: 14
SEQ ID NO: 1            moltype = AA  length = 29
FEATURE                 Location/Qualifiers
source                  1..29
                        mol_type = protein
                        organism = synthetic construct
SEQUENCE: 1
QLEKELQALE KENAQLEWEL QALEKELAQ                                        29

SEQ ID NO: 2            moltype = AA  length = 29
FEATURE                 Location/Qualifiers
source                  1..29
                        mol_type = protein
                        organism = synthetic construct
SEQUENCE: 2
```

-continued

```
QLEKKLQALK KKNAQLKWKL QALKKKLAQ                                      29

SEQ ID NO: 3               moltype = AA  length = 4
FEATURE                    Location/Qualifiers
source                     1..4
                           mol_type = protein
                           organism = synthetic construct
SEQUENCE: 3
GGSG                                                                 4

SEQ ID NO: 4               moltype = AA  length = 6
FEATURE                    Location/Qualifiers
source                     1..6
                           mol_type = protein
                           organism = synthetic construct
SEQUENCE: 4
GSGSGS                                                               6

SEQ ID NO: 5               moltype = AA  length = 8
FEATURE                    Location/Qualifiers
source                     1..8
                           mol_type = protein
                           organism = synthetic construct
SEQUENCE: 5
GGSGGGSG                                                             8

SEQ ID NO: 6               moltype = AA  length = 9
FEATURE                    Location/Qualifiers
source                     1..9
                           mol_type = protein
                           organism = synthetic construct
SEQUENCE: 6
SGGSGGSGG                                                            9

SEQ ID NO: 7               moltype = AA  length = 1590
FEATURE                    Location/Qualifiers
source                     1..1590
                           mol_type = protein
                           organism = synthetic construct
SEQUENCE: 7
MAQWNQLQQL DTRYLEQLHQ LYSDSFPMEL RQFLAPWIES QDWAYAASKE SHATLVFHNL     60
LGEIDQQYSR FLQESNVLYQ HNLRRIKQFL QSRYLEKPME IARIVARCLW EESRLLQTAA    120
TAAQQGGQAN HPTAAVVTEK QQMLEQHLQD VRKRVQDLEQ KMKVVENLQD DFDFNYKTLK    180
SQGDMQDLNG NNQSVTRQKM QQLEQMLTAL DQMRRSIVSE LAGLLSAMEY VQKTLTDEEL    240
ADWKRRQQIA CIGGPPNICL DRLENWITSL AESQLQTRQQ IKKLEELQQK VSYKGDPIVQ    300
HRPMLEERIV ELFRNLMKSA FVVERQPCMP MHPDRPLVIK TGVQFTTKVR LLVKFPELNY    360
QLKIKVCIDK DSGDVAALRG SRKFNILGTN TKVMNMEESN NGSLSAEFKH LTLREQRCGN    420
GGRANCDASL IVTEELHLIT FETEVYHQGL KIDLETHSLP VVVISNICQM PNAWASILWY    480
NMLTNNPKNV NFFTKPPIGT WDQVAEVLSW QFSSTTKRGL SIEQLTTLAE KLLGPGVNYS    540
GCQITWAKFC KENMAGKGFS FWVWLDNIID LVKKYILALW NEGYIMGFIS KERERAILST    600
KPPGTFLLRF SESSKEGGVT FTWVEKDISG KTQIQSVEPY TKQQLNNMSF AEIIMGYKIM    660
DATNILVSPL VYLYPDIPKE EAFGKYCRPE SQEHPEADPG SAAPYLKTKF ICVTPTTCSN    720
TIDLPMSPRT LDSLMQFGNN GEGAEPSAGG QFESLTFDME LTSECATSPM SGGGGSGGGG    780
SGGGGSGGGG SGGGGSMAGW IQAQQLQGDA LRQMQVLYGQ HFPIEVRHYL AQWIESQPWD    840
AIDLDNPQDR AQATQLLEGL VQELQKKAEH QVGEDGFLLK IKLGHYATQL QKTYDRCPLE    900
LVRCIRHILY NEQRLVREAN NCSSPAGILV DAMSQKHLQI NQTFEELRLV TQDTENELKK    960
LQQTQEYFII QYQESLRIQA QFAQLAQLSP QERLSRETAL QQKQVSLEAW LQREAQTLQQ   1020
YRVELAEKHQ KTLQLLRKQQ TIILDDELIQ WKRRQQLAGN GGPPEGSLDV LQSWCEKLAE   1080
IIWQNRQQIR RAEHLCQQLP IPGPVEEMLA EVNATITDII SALVTSTFII EKQPPQVLKT   1140
QTKFAATVRL LVGGKLNVHM NPPQVKATII SEQQAKSLLK NENTRNECSG EILNNCCVME   1200
YHQATGTLSA HFRNMSLKRI KRADRRGAES VTEEKFTVLF ESQFSVGSNE LVFQVKTLSL   1260
PVVVIVHGSQ DHNATATVLW DNAFAEPGRV PFAVPDKVLW PQLCEALNMK FKAEVQSNRG   1320
LTKENLVFLA QKLFNNSSSH LEDYSGLSVS WSQFNRENLP GWNYTFWQWF DGVMEVLKKH   1380
HKPHWNDGAI LGFVNKQQAH DLLINKPDGT FLLRFSDSEI GGITIAWKFD SPERNLWNLK   1440
PFTTRDFSIR SLADRLGDLS YLIYVFPDRP KDEVFSKYYT PVLAKAVDGY VKPQIKQVVP   1500
EFVNASADAG GSSATYMDQA PSPAVCPQAP YNMYPQNPDH VLDQDGEFDL DETMDVARHV   1560
EELLRRPMDS LDSRLSPPAG LFTSARGSLS                                    1590

SEQ ID NO: 8               moltype = AA  length = 1896
FEATURE                    Location/Qualifiers
source                     1..1896
                           mol_type = protein
                           organism = synthetic construct
SEQUENCE: 8
MWTWNAYAFA APSGGGSAQW NQLQQLDTRY LEQLHQLYSD SFPMELRQFL APWIESQDWA     60
YAASKESHAT LVFHNLLGEI DQQYSRFLQE SNVLYQHNLR RIKQFLQSRY LEKPMEIARI    120
VARCLWEESR LLQTAATAAQ QGGQANHPTA AVVTEKQQML EQHLQDVRKR VQDLEQKMKV    180
VENLQDDFDF NYKTLKSQGD MQDLNGNNQS VTRQKMQQLE QMLTALDQMR RSIVSELAGL    240
LSAMEYVQKT LTDEELADWK RRQQIACIGG PPNICLDRLE NWITSLAESQ LQTRQQIKKL    300
```

```
EELQQKVSYK GDPIVQHRPM LEERIVELFR NLMKSAFVVE RQPCMPMHPD RPLVIKTGVQ    360
FTTKVRLLVK FPELNYQLKI KVCIDKDSGD VAALRGSRKF NILGTNTKVM NMEESNNGSL    420
SAEFKHLTLR EQRCGNGGRA NCDASLIVTE ELHLITFETE VYHQGLKIDL ETHSLPVVVI    480
SNICQMPNAW ASILWYNMLT NNPKNVNFFT KPPIGTWDQV AEVLSWQFSS TTKRGLSIEQ    540
LTTLAEKLLG PGVNYSGCQI TWAKFCKENM AGKGFSFWV WLDNIIDLVKK YILALWNEGY    600
IMGFISKERE RAILSTKPPG TFLLRFSESS KEGGVTFTWV EKDISGKTQI QSVEPYTKQQ    660
LNNMSFAEII MGYKIMDATN ILVSPLVYLY PDIPKEEAFG KYCRPESQEH PEADPGSAAP    720
YLKTKFICVT PTTCSNTIDL PMSPRTLDSL MQFGNNGEGA EPSAGGQFES LTFDMELTSE    780
CATSPMSGGG GSGGGGSGGG GSGGGGSGGG GSMAGWIQAQ QLQGDALRQM QVLYGQHFPI    840
EVRHYLAQWI ESQPWDAIDL DNPQDRAQAT QLLEGLVQEL QKKAEHQVGE DGFLLKIKLG    900
HYATQLQKTY DRCPLELVRC IRHILYNEQR LVREANNCSS PAGILVDAMS QKHLQINQTF    960
EELRLVTQDT ENELKKLQQT QEYFIIQYQE SLRIQAQFAQ LAQLSPQERL SRETALQQKQ   1020
VSLEAWLQRE AQTLQQYRVE LAEKHQKTLQ LLRKQQTIIL DDELIQWKRR QQLAGNGGPP   1080
EGSLDVLQSW CEKLAEIIWQ NRQQIRRAEH LCQQLPIPGP VEEMLAEVNA TITDIISALV   1140
TSTFIIEKQP PQVLKTQTKF AATVRLLVGG KLNVHMNPPQ VKATIISEQQ AKSLLKNENT   1200
RNECSGEILN NCCVMEYHQA TGTLSAHFRN MSLKRIKRAD RRGAESVTEE KFTVLFESQF   1260
SVGSNELVFQ VKTLSLPVVV IVHGSQDHNA TATVLWDNAF AEPGRVPPAV PDKVLWPQLC   1320
EALNMKFKAE VQSNRGLTKE NLVFLAQKLF NNSSSHLEDY SGLSVSWSQF NRENLPGWNY   1380
TFWQWFDGVM EVLKKHHKPH WNDGAILGFV NKQQAHDLLI NKPDGTFLLR FSDSEIGGIT   1440
IAWKFDSPER NLWNLKPFTT RDFSIRSLAD RLGDLSYLIY VFPDRPKDEV FSKYYTPVLA   1500
KAVDGYVKPQ IKQVVPEFVN ASADAGGSSA TYMDQAPSPA VCPQAPYNMY PQNPDHVLDQ   1560
DGEFDLDETM DVARHVEELL RRPMDSLDSR LSPPAGLFTS ARGSLSEGRG SLLTCGDVEE   1620
NPGPMGCGCS SHPELEAEAA AKEAAAKEAA AKEAAAKEALE AEAAAKEAAA KEAAAKEAAA   1680
KALESGGGSM SRLDKSKVIN SALELLNEVG IEGLTTRKLA QKLGVEQPTL YWHVKNKRAL   1740
LDALAIEMLD RHHTHFCPLE GESWQDFLRN NAKSFRCALL SHRDGAKVHL GTRPTEKQYE   1800
TLENQLAFLC QQGFSLENAL YALSAVGHFT LGCVLEDQEH QVAKEERETP TTDSMPPLLR   1860
QAIELFDHQG AEPAFLFGLE LIICGLEKQL KCESGS                             1896

SEQ ID NO: 9              moltype = AA  length = 2729
FEATURE                   Location/Qualifiers
source                    1..2729
                          mol_type = protein
                          organism = synthetic construct
SEQUENCE: 9
MPDPAAHLPF FYGSISRAEA EEHLKLAGMA DGLFLLRQCL RSLGGYVLSL VHDVRFHHFP     60
IERQLNGTYA IAGGKAHCGP AELCEFYSRD PDGLPCNLRK PCNRPSGLEP QPGVFDCLRD    120
AMVRDYVRQT WKLEGEALEQ AIISQAPVEE KLIATTAHER MPWYHSSLTR EEAERKLYSG    180
AQTDLKFLLR PRKEQGTYAL SLIYGKTVYH YLISQDKAGK YCIPEGTKFD TLWQLVEYLK    240
LKADGLIYCL KEACPNSSAS NASGAAAPTL PAHPSTLTHP SGGGGSSLFK GPRDYNPISS    300
TICHLTNESD GHTTSLYGIG FGPFIITNKH LFRRNNGTLL VQSLHGVFKV KNTTTLQQHL    360
IDGRDMIIIR MPKDFPPFPQ KLKFREPQRE ERICLVTTNF QTKSMSSMVS DTSCTFPSSD    420
GIFWKHWIQT KDGQCGSPLV STRDGFIVGI HSASNFTNTN NYFTSVPKNF MELLTNQEAQ    480
QWVSGWRLNA DSVLWGGHKV FMSKPEEPFQ PVKEATQLMN ELVYSQEGRG SLLTCGDVEE    540
NPGPMGCGCS SHPESGGGGS GGGGSENLYF QGENLYFQGE NLYFQGENLY FQGENLYFQG    600
ENLYFQGENL YFQGENLYFQ GENLYFQGAQ WNQLQQLDTR YLEQLHQLYS DSFPMELRQF    660
LAPWIESQDW AYAASKESHA TLVFHNLLGE IDQQYSRFLQ ESNVLYQHNL RRIKQFLQSR    720
YLEKPMEIAR IVARCLWEES RLLQTAATAA QGGQANHPT AAVVTEKQQM LEQHLQDVRK    780
RVQDLEQKMK VVENLQDDFD FNYKTLKSQG DMQDLNGNNQ SVTRQKMQQL EQMLTALDQM    840
RRSIVSELAG LLSAMEYVQK TLTDEELADW KRRQQIACIG GPPNICLDRL ENWITSLAES    900
QLQTRQQIKK LEELQQKVSY KGDPIVQHRP MLEERIVELF RNLMKSAFVV ERQPCMPMHP    960
DRPLVIKTGV QFTTKVRLLV KFPELNYQLK IKVCIDKDSG DVAALRGSRK FNILGTNTKV   1020
MNMEESNNGS LSAEFKHLTL REQRCGNGGR ANCDASLIVT EELHLITFET EVYHQGLKID   1080
LETHSLPVVV ISNICQMPNA WASILWYNML TNNPKNVNFF TKPPIGTWDQ VAEVLSWQFS   1140
STTKRGLSIE QLTTLAEKLL GPGVNYSGCQ ITWAKFCKEN MAGKGFSFWV WLDNIIDLVK   1200
KYILALWNEG YIMGFISKER ERAILSTKPP GTFLLRFSES SKEGGVTFTW VEKDISGKTQ   1260
IQSVEPYTKQ QLNNMSFAEI IMGYKIMDAT NILVSPLVYL YPDIPKEEAF GKYCRPESQE   1320
HPEADPGSAA PYLKTKFICV TPTTCSNTID LPMSPRTLDS LMQFGNNGEG AEPSAGGQFE   1380
SLTFDMELTS ECATSPMSGG GGSGGGGSGG GGSGGGGSGG GGSMAGWIQA QQLQGDALRQ   1440
MQVLYGQHFP IEVRHYLAQW IESQPWDAID LDNPQDRAQA TQLLEGLVQE LQKKAEHQVG   1500
EDGFLLKIKL GHYATQLQKT YDRCPLELVR CIRHILYNEQ RLVREANNCS SPAGILVDAM   1560
SQKHLQINQT FEELRLVTQD TENELKKLQQ TQEYFIIQYQ ESLRIQAQFA QLAQLSPQER   1620
LSRETALQQK QVSLEAWLQR EAQTLQQYRV ELAEKHQKTL QLLRKQQTII LDDELIQWKR   1680
RQQLAGNGGP PEGSLDVLQS WCEKLAEIIW QNRQQIRRAE HLCQQLPIPG PVEEMLAEVN   1740
ATITDIISAL VTSTFIIEKQ PPQVLKTQTK FAATVRLLVG GKLNVHMNPP QVKATIISEQ   1800
QAKSLLKNEN TRNECSGEIL NNCCVMEYHQ ATGTLSAHFR NMSLKRIKRA DRRGAESVTE   1860
EKFTVLFESQ FSVGSNELVF QVKTLSLPVV VIVHGSQDHN ATATVLWDNA FAEPGRVPFA   1920
VPDKVLWPQL CEALNMKFKA EVQSNRGLTK ENLVFLAQKL FNNSSSHLED YSGLSVSWSQ   1980
FNRENLPGWN YTFWQWFDGV MEVLKKHHKP HWNDGAILGF VNKQQAHDLL INKPDGTFLL   2040
RFSDSEIGGI TIAWKFDSPE RNLWNLKPFT TRDFSIRSLA DRLGDLSYLI YVFPDRPKDE   2100
VFSKYYTPVL AKAVDGYVKP QIKQVVPEFV NASADAGGSS ATYMDQAPSP AVCPQAPYNM   2160
YPQNPDHVLD QDGEFDLDET MDVARHVEEL LRRPMDSLDS RLSPPAGLFT SARGSLSEGR   2220
GSLLTCGDVE ENPGPMETDT LLLWVLLLWV PGSTGDIQMT QTTSSLSASL GDRVTISCRA   2280
SQDISKYLNW YQQKPDGTVK LLIYHTSRLH SGVPSRFSGS GSGTDYSLTI SNLEQEDIAT   2340
YFCQQGNTLP YTFGGGTKLE ITKAGGGSG GGGSGGGGSG GGSDEVKLQE SGPGLVAPSQ    2400
SLSVTCTVSG VSLPDYGVSW IRQPPRKGLE WLGVIWGSET TYYNSALKSR LTIIKDNSKS   2460
QVFLKMNSLQ TDDTAIYYCA KHYYGGSYA MDYWGQGTSV TVSSDPTTTP APRPPTPAPT   2520
IASQPLSLRP EACRPAAGGA VHTRGLDFAC DIYIWAPLAG TCGVLLLSLV ITLYCKRGRK   2580
KLLYIFKQPF MRPVQTTQEE DGCSCRFPEE EEGGCELRVK FSRSADAPAY QQGQNQLYNE   2640
LNLGRREEYD VLDKRRGRDP EMGGKPRRKN PQEGLYNELQ KDKMAEAYSE IGMKGERRRG   2700
```

```
KGHDGLYQGL STATKDTYDA LHMQALPPR                                              2729

SEQ ID NO: 10              moltype = AA  length = 2430
FEATURE                    Location/Qualifiers
source                     1..2430
                           mol_type = protein
                           organism = synthetic construct
SEQUENCE: 10
MWTWNAYAFA APSGGGSMPD PAAHLPFFYG SISRAEAEEH LKLAGMADGL FLLRQCLRSL            60
GGYVLSLVHD VRFHHFPIER QLNGTYAIAG GKAHCGPAEL CEFYSRDPDG LPCNLRKPCN           120
RPSGLEPQPG VFDCLRDAMV RDYVRQTWKL EGEALEQAII SQAPQVEKLI ATTAHERMPW           180
YHSSLTREEA ERKLYSGAQT DGKFLLRPRK EQGTYALSLI YGKTVYHYLI SQDKAGKYCI           240
PEGTKFDTLW QLVEYLKLKA DGLIYCLKEA CPNSSASNAS GAAAPTLPAH PSTLTHPSGG           300
GGSSLFKGPR DYNPISSTIC HLTNESDGHT TSLYGIGFGP FIITNKHLFR RNNGTLLVQS           360
LHGVFKVKNT TTLQQHLIDG RDMIIIRMPK DFPPFPQKLK FREPQREERI CLVTTNFQTK           420
SMSSSMVSDTS CTFPSSDGIF WKHWIQTKDG QCGSPLVSTR DGFIVGIHSA SNFTNTNNYF          480
TSVPKNFMEL LTNQEAQQWV SGWRLNADSV LWGGHKVFMS KPEEPFQPVK EATQLMNELV           540
YSQEGRGSLL TCGDVEENPG PMETDTLLLW VLLLWVPGST GDSSGKPIPN PLLGLDSSGG           600
GSAPRDVRVR KIKPLSEIHS GNSVSLQCDF SSSHPKEVQF FWEKNGRLLG KESQLNFDSI           660
SPEDAGSYSC WVNNSIGQTA SKAWTLEVLY APRRLRVSMS PGDQVMEGKS ATLTCESDAN           720
PPVSHYTWFD WNNQSLPYHS QKLRLEPVKV QHSGAYWCQG TNSVGKGRSP LSTLTVYYSP           780
ETIGRRAVTL AYLIFCLCSL VGILHLRARR SMDEANQPLL CPQCYAEE YEKLQNPNQS             840
VVGGSGGSMS RLDKSKVINS ALELLNEVGI EGLTTRKLAQ KLGVEQPTLY WHVKNKRALL           900
DALAIEMLDR HHTHFCPLEG ESWQDFLRNN AKSFRCALLS HRDGAKVHLG TRPTEKQYET           960
LENQLAFLCQ QGFSLENALY ALSAVGHFTL GCVLEDQEHQ VAKEERETPT TDSMPPLLRQ          1020
AIELFDHQGA EPAFLFGLEL IICGLEKQLK CESGSEGRGS LLTCGDVEEN PGPMETDTLL          1080
LWVLLLWVPG STGDIQMTQT TSSLSASLGD RVTISCRASQ DISKYLNWYQ QKPDGTVKLL          1140
IYHTSRLHSG VPSRFSGSGS GTDYSLTISN LEQEDIATYF CQQGNTLPYT FGGGTKLEIT          1200
KAGGGGSGGG GSGGGGSGGG GSEVKLQESG PGLVAPSQSL SVTCTVSGVS LPDYGVSWIR          1260
QPPRKGLEWL GVIWGSETTY YNSALKSRLT IIKDNSKSQV FLKMNSLQTD DTAIYYCAKH          1320
YYYGGSYAMD YWGQGTSVTV SSDPTTTPAP RPPTPAPTIA SQPLSLRPEA CRPAAGGAVH          1380
TRGLDFACDI YIWAPLAGTC GVLLLSLVIT LYCKRGRKKL LYIFKQPFMR PVQTTQEEDG          1440
CSCRFPEEEE GGCELRVKFS RSADAPAYQQ GQNQLYNELN LGRREEYDVL DKRRGRDPEM          1500
GGKPRRKNPQ EGLYNELQKD KMAEAYSEIG MKGERRRGKG HDGLYQGLST ATKDTYDALH          1560
MQALPPRGGS GGSENLYFQG ENLYFQGENL YFQGENLYFQ GENLYFQGEN LYFQGENLYF          1620
QGENLYFQGE NLYFQGMAGW IQAQQLQGDA LRQMQVLYGQ HPFIEVRHYL AQWIESQPWD          1680
AIDLDNPQDR AQATQLLEGL VQELQKKAEH QVGEDGFLLK IKLGHYATQL QKTYDRCPLE          1740
LVRCIRHILY NEQRLVREAN NCSSPAGILV DAMSQKHLQI NQTFEELRLV TQDTENELKK          1800
LQQTQEYFII QYQESLRIQA QFAQLAQLSP QERLSRETAL QQKQVSLEAW LQREAQTLQQ          1860
YRVELAEKHQ KTLQLLRKQQ TIILDDELIQ WKRRQQLAGN GGPPEGSLDV LQSWCEKLAE          1920
IIWQNRQQIR RAEHLCQQLP IPGPVEEMLA EVNATITDII SALVTSTFII EKQPPQVLKT          1980
QTKFAATVRL LVGGKLNVHM NPPQVKATII SEQQAKSLLK NENTRNECSG EILNNCCVME          2040
YHQATGTLSA HFRNMSLKRI KRADRRGAES VTEEKFTVLF ESQFSVGSNE LVFQVKTLSL          2100
PVVVIVHGSQ DHNATATVLW DNAFAEPGRV PFAVPDKVLW PQLCEALNMK FKAEVQSNRG          2160
LTKENLVFLA QKLFNNSSSH LEDYSGLSVS WSQFNRENLP GWNYTFWQWF DGVMEVLKKH          2220
HKPHWNDGAI LGFVNKQQAH DLLLINKPDGT FLLRFSDSEI GGITIAWKFD SPERNLWNLK         2280
PFTTRDFSIR SLADRLGDLS YLIYVFPDRP KDEVFSKYYT PVLAKAVDGY VKPQIKQVVP          2340
EFVNAFADAG GSSATYMDQA PSPAVCPQAP YNMYPQNPDH VLDQDGEFDL DETMDVARHV          2400
EELLRRPMDS LDSRLSPPAG LFTSARGSLS                                          2430

SEQ ID NO: 11              moltype = AA  length = 1813
FEATURE                    Location/Qualifiers
source                     1..1813
                           mol_type = protein
                           organism = synthetic construct
SEQUENCE: 11
ILWHEMWHEG LEEASRLYFG ERNVKGMFEV LEPLHAMMER GPQTLKETSF NQAYGRDLME            60
AQEWCRKYMK SGNVKDLLQA WDLYYHVFRR ISKSGGGGSG GGGSGGGGSM AGWIQAQQLQ           120
GDALRQMQVL YGQHPFIEVR HYLAQWIESQ PWDAIDLDNP QDRAQATQLL EGLVQELQKK           180
AEHQVGEDGF LLKIKLGHYA TQLQKTYDRC PLELVRCIRH ILYNEQRLVR EANNCSSPAG           240
ILVDAMSQKH LQINQTFEEL RLVTQDTENE LKKLQQTQEY FIIQYQESLR IQAFQAQLAQ           300
LSPQERLSRE TALQQKQVSL EAWLQREAQT LQQYRVELAE KHQKTLQLLR KQQTIILDDE           360
LIQWKRRQQL AGNGGPPEGS LDVLQSWCEK LAEIIWQNRQ QIRRAEHLCQ QLPIPGPVEE           420
MLAEVNATIT DIISALVTST FIIEKQPPQV LKTQTKFAAT VRLLVGGKLN VHMNPPQVKA           480
TIISEQQAKS LLKNENTRNE CSGEILNNCC VMEYHQATGT LSAHFRNMSL KRIKRADRRG           540
AESVTEEKFT VLFESQFSVG SNELVFQVKT LSLPVVVIVH GSQDHNATAT VLWDNAFAEP           600
GRVPFAVPDK VLWPQLCEAL NMKFKAEVQS NRGLTKENLV FLAQKLFNNS SSHLEDYSGL           660
SVSWSQFNRE NLPGWNYTFW QWFDGVMEVL KKHHKPHWND GAILGFVNKQ QAHDLLINKP           720
DGTFLLRFSD SEIGGITIAW KFDSPERNLW NLKPFTTRDF SIRSLADRLG DLSYLIYVFP           780
DRPKDEVFSK YYTPVLAKAV DGYVKPQIKQ VVPEFVNASA DAGGSSATYM DQAPSPAVCP           840
QAPYNMYPQN PDHVLDQDGE FDLDETMDVA RHVEELLRRP MDSLDSRLSP PAGLFTSARG           900
SLSEGRGSLL TCGDVEENPG PGVQVETISP GDGRTFPKRG QTCVVHYTGM LEDGKKVDSS           960
RDRNKPFKFM LGKQEVIRGW EEGVAQMSVG QRAKLTISPD YAYGATGHPG IIPPHATLVF          1020
DVELLKLESG GGGSGGGGSG GGSAQWNQLQ QLDTRYLEQ LHQLYSDSFP MELRQFLAPW           1080
IESQDWAYAA SKESHATLVF HNLLGEIDQQ YSRFLQESNV LYQHNLRRIK QFLQSRYLEK          1140
PMEIARIVAR CLWEESRLLQ TAATAAQQGG QANHPTAAVV TEKQQMLEQH LQDVRKRVQD          1200
LEQKMKVVEN LQDDFDFNYK TLKSQGDMQD LNGNNQSVTR QKMQQLEQML TALDQMRRSI          1260
VSELAGLLSA MEYVQKTLTD EELADWKRRQ QIACIGGPPN ICLDRLENWI TSLAESQLQT          1320
RQQIKKLEEL QQKVSYKGDP IVQHRPMLEE RIVELFRNLM KSAFVVERQP CMPMHPDRPL          1380
```

```
                                                   -continued
VIKTGVQFTT KVRLLVKFPE LNYQLKIKVC IDKDSGDVAA LRGSRKFNIL GTNTKVMNME  1440
ESNNGSLSAE FKHLTLREQR CGNGGRANCD ASLIVTEELH LITFETEVYH QGLKIDLETH  1500
SLPVVVISNI CQMPNAWASI LWYNMLTNNP KNVNFFTKPP IGTWDQVAEV LSWQFSSTTK  1560
RGLSIEQLTT LAEKLLGPGV NYSGCQITWA KFCKENMAGK GFSFWVWLDN IIDLVKKYIL  1620
ALWNEGYIMG FISKERERAI LSTKPPGTFL LRFSESSKEG GVTFTWVEKD ISGKTQIQSV  1680
EPYTKQQLNN MSFAEIIMGY KIMDATNILV SPLVYLYPDI PKEEAFGKYC RPESQEHPEA  1740
DPGSAAPYLK TKFICVTPTT CSNTIDLPMS PRTLDSLMQF GNNGEGAEPS AGGQFESLTF  1800
DMELTSECAT SPM                                                    1813

SEQ ID NO: 12          moltype = AA  length = 1832
FEATURE                Location/Qualifiers
source                 1..1832
                       mol_type = protein
                       organism = synthetic construct
SEQUENCE: 12
MWTWNAYAFA APSGGGGSGG GGSGGGGSMA GWIQAQQLQG DALRQMQVLY GQHFPIEVRH   60
YLAQWIESQP WDAIDLDNPQ DRAQATQLLE GLVQELQKKA EHQVGEDGFL LKIKLGHYAT  120
QLQKTYDRCP LELVRCIRHI LYNEQRLVRE ANNCSSPAGI LVDAMSQKHL QINQTFEELR  180
LVTQDTENEL KKLQQTQEYF IIQYQESLRI QAQFAQLAQL SPQERLSRET ALQQKQVSLE  240
AWLQREAQTL QQYRVELAEK HQKTLQLLRK QQTIILDDEL IQWKRRQQLA GNGGPPEGSL  300
DVLQSWCEKL AEIIWQNRQQ IRRAEHLCQQ LPIPGPVEEM LAEVNATITD IISALVTSTF  360
IIEKQPPQVL KTQTKFAATV RLLVGGKLNV HMNPPQVKAT IISEQQAKSL LKNENTRNEC  420
SGEILNNCCV MEYHQATGTL SAHFRNMSLK RIKRADRRGA ESVTEEKFTV LFESQFSVGS  480
NELVFQVKTL SLPVVVIVHG SQDHNATATV LWDNAFAEPG RVPFAVPDKV LWPQLCEALN  540
MKFKAEVQSN RGLTKENLVF LAQKLFNNSS SHLEDYSGLS VSWSQFNREN LPGWNYTFWQ  600
WFDGVMEVLK KHHKPHWNDG AILGFVNKQQ AHDLLINKPD GTFLLRFSDS EIGGITIAWK  660
FDSPERNLWN LKPFTTRDFS IRSLADRLGD LSYLIYVFPD RPKDEVFSKY YTPVLAKAVD  720
GYVKPQIKQV VPEFVNASAD AGGSSATYMD QAPSPAVCPQ APYNMYPQNP DHVLDQDGEF  780
DLDETMDVAR HVEELLRRPM DSLDSRLSPP AGLFTSARGS LSEGRGSLLT CGDVEENPGP  840
MSRLDKSKVI NSALELLNEV GIEGLTTRKL AQKLGVEQPT LYWHVKNKRA LLDALAIEML  900
DRHHTHFCPL EGESWQDFLR NNAKSFRCAL LSHRDGAKVH LGTRPTEKQY ETLENQLAFL  960
CQQGFSLENA LYALSAVGHF TLGCVLEDQE HQVAKEERET PTTDSMPPLL RQAIELFDHQ 1020
GAEPAFLFGL ELIICGLEKQ LKCESGSSGG GGSGGGGSGG GGSAQWNQLQ QLDTRYLEQL 1080
HQLYSDSFPM ELRQFLAPWI ESQDWAYAAS KESHATLVFH NLLGEIDQQY SRFLQESNVL 1140
YQHNLRRIKQ FLQSRYLEKP MEIARIVARC LWEESRLLQT AATAAQQGGQ ANHPTAAVVT 1200
EKQQMLEQHL QDVRKRVQDL EQKMKVVENL QDDFDFNYKT LKSQGDMQDL NGNNQSVTRQ 1260
KMQQLEQMLT ALDQMRRSIV SELAGLLSAM EYVQKTLTDE ELADWKRRQQ IACIGGPPNI 1320
CLDRLENWIT SLAESQLQTR QQIKKLEELQ QKVSYKGDPI VQHRPMLEER IVELFRNLMK 1380
SAFVVERQPC MPMHPDRPLV IKTGVQFTTK VRLLVKFPEL NYQLKIKVCI DKDSGDVAAL 1440
RGSRKFNILG TNTKVMNMEE SNNGSLSAEF KHLTLREQRC GNGGRANCDA SLIVTEELHL 1500
ITFETEVYHQ GLKIDLETHS LPVVVISNIC QMPNAWASIL WYNMLTNNPK NVNFFTKPPI 1560
GTWDQVAEVL SWQFSSTTKR GLSIEQLTTL AEKLLGPGVN YSGCQITWAK FCKENMAGKG 1620
FSFWVWLDNI IDLVKKYILA LWNEGYIMGF ISKERERAIL STKPPGTFLL RFSESSKEGG 1680
VTFTWVEKDI SGKTQIQSVE PYTKQQLNNM SFAEIIMGYK IMDATNILVS PLVYLYPDIP 1740
KEEAFGKYCR PESQEHPEAD PGSAAPYLKT KFICVTPTTC SNTIDLPMSP RTLDSLMQFG 1800
NNGEGAEPSA GGQFESLTFD MELTSECATS PM                               1832

SEQ ID NO: 13          moltype =    length =
SEQUENCE: 13
000

SEQ ID NO: 14          moltype = AA  length = 7
FEATURE                Location/Qualifiers
source                 1..7
                       mol_type = protein
                       organism = synthetic construct
SEQUENCE: 14
ENLYFQS                                                              7
```

The invention claimed is:

1. A cytolytic immune cell which comprises a CAR and an inducible Signal Transducer and Activator of Transcription (STAT) molecule,
    wherein
    (a) the STAT molecule comprises a first polypeptide comprising a first dimerizing domain (DD) and a second polypeptide comprising a second DD, which second DD specifically binds to the first DD; and wherein the presence of an agent causes dimerization of the first and second DD and induces activation of the STAT molecule, or
    (b) the STAT molecule comprises a first polypeptide comprising a first dimerizing domain (DD) and a second polypeptide comprising a second DD, which second DD specifically binds to the first DD; and
    wherein the presence of an agent causes dissociation of the first and second DD and induces non-activation of the STAT molecule.

2. A cell according to claim 1 (a), wherein the first DD comprises FRB and the second DD comprises FKBP12 and the agent is rapamycin.

3. A cell according to claim 1 (b), wherein the first DD comprises Tet Repressor Protein (TetR) and the second DD comprises Transcription Inducing Peptide (TiP); and the agent is tetracycline, doxycycline or minocycline.

4. A pharmaceutical composition comprising a plurality of cells according to claim 1.

5. A pharmaceutical composition according to claim 4 for use in treating and/or preventing a disease.

* * * * *